United States Patent
Continetti et al.

(10) Patent No.: US 10,453,668 B2
(45) Date of Patent: Oct. 22, 2019

(54) SPECTROMETRY METHOD AND SPECTROMETER DEVICE

(71) Applicant: The Regents of the University of California, Oakland, CA (US)

(72) Inventors: Robert Continetti, La Jolla, CA (US); Morgan Miller, La Jolla, CA (US); Brian Adamson, La Jolla, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 15/907,786

(22) Filed: Feb. 28, 2018

(65) Prior Publication Data

US 2018/0247805 A1    Aug. 30, 2018

Related U.S. Application Data

(60) Provisional application No. 62/464,851, filed on Feb. 28, 2017.

(51) Int. Cl.
*H01J 49/42* (2006.01)
*H01J 49/16* (2006.01)
(Continued)

(52) U.S. Cl.
CPC .......... *H01J 49/4245* (2013.01); *G01N 15/10* (2013.01); *H01J 49/0031* (2013.01);
(Continued)

(58) Field of Classification Search
CPC .. H01J 49/4245; H01J 49/0031; H01J 49/165; H01J 2237/1207; H05H 5/06; H05H 9/00
(Continued)

(56) References Cited

U.S. PATENT DOCUMENTS

| | | | |
|---|---|---|---|
| 9,744,490 B1* | 8/2017 | Novosselov | B01D 45/16 |
| 2015/0076340 A1* | 3/2015 | Liang | H01J 49/164 250/282 |
| 2018/0005809 A1* | 1/2018 | Roukes | H01J 49/061 |

OTHER PUBLICATIONS

W. Henry Benner, "A Gated Electrostatic Ion Trap to Repetitiously Measure the Charge and m/z of Large Electrospray Ions", Analytical Chemistry, vol. 69, No. 20, pp. 4162-4168, Oct. 15, 1997.

(Continued)

*Primary Examiner* — Nicole M Ippolito
(74) *Attorney, Agent, or Firm* — Greer, Burns & Crain, Ltd.; Steven P. Fallon

(57) ABSTRACT

A spectrometer device for analysis of aerosol particles, dusts, and other microparticles and/or nanoparticles includes an electrospray ionization source supplying a particle stream to an aerodynamic lens that focuses and collimates a beam of particles. An electrostatic trap accepts the beam of particles and traps a single trapped particle at a time in the electrostatic trap to oscillate with a measurable amplitude and frequency. A sensor senses the amplitude and frequency, and a processor determines a calculated mass to charge ratio from the amplitude and frequency of oscillation of the trapped particle in real time. A method creates a focused stream of micro or nanoparticles, traps a single particle at a time in an electrostatic trap. The amplitude and frequency of the oscillation of the trapped particle is sensed. The mass to charge ratio is determined from the amplitude and frequency of oscillation. Particles can be accelerated into a target.

19 Claims, 17 Drawing Sheets

(51) Int. Cl.
  *H01J 49/00* (2006.01)
  *H05H 5/06* (2006.01)
  *G01N 15/10* (2006.01)
  *H05H 9/00* (2006.01)
  *G01N 15/00* (2006.01)

(52) U.S. Cl.
  CPC ............. *H01J 49/165* (2013.01); *H05H 5/06* (2013.01); *G01N 2015/0046* (2013.01); *G01N 2015/1043* (2013.01); *H01J 2237/1207* (2013.01); *H05H 9/00* (2013.01)

(58) Field of Classification Search
  USPC .................................. 250/281, 282, 283, 288
  See application file for complete search history.

(56) References Cited

OTHER PUBLICATIONS

Nathan C. Contino et al., "Charge Detection Mass Spectrometry with Resolved Charge States", Journal of American Society of Mass Spectrometry, vol. 24, pp. 101-108, Nov. 30, 2012.

M. Dahan et al., "A new type of electrostatic ion trap for storage of fast ion beams", Review of Scientific Instruments, vol. 69, No. 1, pp. 76-83, Jan. 1998.

David A. Dahl, "SIMION for the personal computer in reflection", International Journal of Mass Spectrometry 200, pp. 3-25, 2000.

Barton Dahneke, "Further Measurements of the Bouncing of Small Latex Spheres", Journal of Colloid and Interface Science, vol. 51, No. 1, pp. 58-65, Apr. 1975.

Barton Dahneke, "Particle Bounce or Capture-Search for an Adequate Theory: I. Conservation-of-Energy Model for a Simple Collision Process", Aerosol Science and Technology, vol. 23, No. 1, pp. 25-39, Jun. 12, 2007.

J.F. Friichtenicht, "Micrometeroid Simulation Using Nuclear Accelerator Techniques", Nuclear Instruments and Methods, vol. 28, pp. 70-78, 1964.

J.F. Friichtenicht, "Two-Million Volt Electrostatic Accelerator for Hypervelocity Research", Review of Scientific Instruments, vol. 33, No. 2, pp. 209-212, Feb. 1962.

Stephen D. Fuerstenau and W. Henry Benner, "Molecular Weight Determination of Megadalton DNA Electrospray Ions Using Charge Detection Time-of-flight Mass Spectrometry", Rapid Communications in Mass Spectrometry, vol. 9, pp. 1528-1538, 1995.

Manuel Gamero-Castano, "Induction charge detector with multiple sensing stages", Review of Scientific Instruments, vol. 78, 043301, Apr. 11, 2007.

E. Hendell and U. Even, "Tabletop linear accelerator for massive molecules", Review of Scientific Instruments, vol. 66, No. 7, pp. 3901-3902, Jul. 1995.

Yun-Fei Hsu et al., "Macromolecular Ion Accelerator", Analytical Chemistry, vol. 84, pp. 5765-5769, 2012.

Christopher J. Johnson et al., "Photoelectron-photofragment coincidence spectroscopy in a cryogenically cooled linear electrostatic ion beam trap", Review of Scientific Instruments, vol. 82, 105105, Oct. 10, 2011.

David Z. Keifer et al., "Charge Detection Mass Spectrometry with Almost Perfect Charge Accuracy", Analytical Chemistry, vol. 87, pp. 10330-10337, Sep. 29, 2015.

David Z. Keifer and Martin F. Jarrold, "Single-Molecule Mass Spectrometry", Mass Spectrometry Reviews, vol. 36, pp. 715-733, Feb. 12, 2016.

Peng Liu et al., "Generating Particle Beams of Controlled Dimensions and Divergence: I. Theory of Particle Motion in Aerodynamic Lenses and Nozzle Expansions", Aerosol Science and Technology, vol. 22, No. 3, pp. 293-313, 1995.

S. Ring et al., "Fourier Transform Time-of-Flight Mass Spectrometry in an Electrostatic Ion Beam Trap", Analytical Chemistry, vol. 72, No. 17, pp. 4041-4046, Sep. 1, 2000.

James F. Vedder, "Microparticle accelerator of unique design", Review of Scientific Instruments, vol. 49, No. 1, pp. 1-7, Jan. 1978.

Xiaoliang Wang and Peter H. McMurry, "A Design Tool for Aerodynamic Lens Systems", Aerosol Science and Technology, vol. 40, No. 5, pp. 320-334, Feb. 23, 2007.

D. Zajfman et al., "Electrostatic bottle for long-time storage of fast ion beams", Physical Review A, vol. 55, No. 3, Mar. 1997.

* cited by examiner

SPECTROMETRY METHOD AND SPECTROMETER DEVICE

PRIORITY CLAIM AND REFERENCE TO RELATED APPLICATION

The application claims priority under 35 U.S.C. § 119 from prior provisional application Ser. No. 62/464,851, which was filed Feb. 28, 2017.

STATEMENT OF GOVERNMENT INTEREST

This invention was made with government support under contract no. CHE 1229690 awarded by the National Science Foundation. The government has certain rights in the invention.

FIELD

Fields of the invention include mass spectrometry, the measurement of mass and charge of particles, aerosols and dusts, including nano sized to micron sized particles.

BACKGROUND

Interest in the characterization of nanoparticles, aerosols and dusts continues to increase, but typical tools and devices are not capable of manipulation and analysis of single particles. Fields ranging from atmospheric chemistry to astrophysical phenomena to industrial applications would benefit from tools to analyze particles with the capability of analyzing single particles and their impact dynamics.

Much early research focused on theoretical modeling of nanoparticle and microparticle collisions. Electrostatic accelerators were then recognized as a tool to manipulate small, easily charged microparticles. An early electrostatic accelerator for microparticle study was a 2 MV van de Graaff dust accelerator was described and shown to accelerate 1 μm particles to ~6 km/s. See, e.g., Friichtenicht J F., "Two-million-volt electrostatic accelerator for hypervelocity research," Rev Sci Instrum. 1962; 33:209-12. Friichtenicht J F. Micrometeoroid simulation using nuclear accelerator techniques. Nucl Inst Meth. 1964; 28:70-8. One early example of a switched, multistage linear accelerator for microparticles is described by Vedder. Vedder J F, "Microparticle accelerator of unique design," Rev Sci Instrum. 1978; 49:1-7. Such microparticle accelerators benefitted from advances in laboratory-scale linear accelerators, such as the accelerator described by Hendell and Even. Hendell E, Even U. Tabletop linear accelerator for massive molecules. Rev Sci Instrum. 1995; 66:3901-2.

Mass spectrometric measurements on single charged nanoparticles can be conducted via charge detection mass spectrometry (CDMS) techniques. Benner W H., "A gated electrostatic ion trap to repetitiously measure the charge and m/z of large electrospray ions," Anal Chem. 1997; 69:4162-8. CDMS determines the absolute charge on a particle from the magnitude of the image charge induced on a pickup electrode when a charged particle passes through. The image charge waveform also yields the particle time-of-flight (TOF) and velocity through the pickup providing the mass-to-charge ratio for fixed energy particles. Gamero-Castaño M. Induction charge detector with multiple sensing stages. Rev Sci Instrum. 2007; 78:043301. State-of-the-art CDMS is capable of analysis of massive biomolecules, cells and nanoparticles, and can also conduct mass spectrometry measurements. See, e.g., Contino N C, Pierson E E, Keifer D Z, Jarrold M F, "Charge detection mass spectrometry with resolved charge states," J Am Soc Mass Spec. 2013; 24:101-8. Keifer D Z, Shinholt D L, Jarrold M F, "Charge detection mass spectrometry with almost perfect charge accuracy," Anal Chem. 2015; 87:10330-7; Keifer D Z, Jarrold M F, "Single-molecule mass spectrometry," Mass Spec Rev. Volume 414, March 2017, Pages 45-55 (2016). As shown by Hendell and Even (Hendell E, Even U., "Tabletop linear accelerator for massive molecules," Rev Sci Instrum. 1995; 66:3901-2), and later applied by Hsu and colleagues (Hsu Y-F, Lin J-L, Lai S-H, Chu M-L, Wang Y-S, Chen C-H. Macromolecular Ion Accelerator. Anal Chem. 2012; 84:5765-9), a linear accelerator for large molecular ions can be configured using modern high-voltage MOSFET switching techniques.

SUMMARY OF THE INVENTION

An embodiment of the invention is a spectrometer device for analysis of aerosol particles, dusts, and other microparticles and/or nanoparticles. The device includes an electrospray ionization source supplying a particle stream to an aerodynamic lens that focuses and collimates a beam of particles. An electrostatic trap with entrance and exit mirrors is configured and controlled to accept the beam of particles and trap a single trapped particle at a time in the electrostatic trap to oscillate with a measurable amplitude and frequency. A sensor senses the amplitude and frequency, and a processor determines a calculated mass to charge ratio from the amplitude and frequency of oscillation of the trapped particle in real time. The processor preferably and in real-time adjusts the trap to re-calibrate continuously by injecting charge into an image charge detector tube of the trap.

The electrospray ionization source is preferably fully enclosed in a controlled atmosphere. The electrostatic trap can be cooled to control the phase of the trapped particle. The aerodynamic lens can include a series of apertures machined to particular size and finish. A charge detector after the aerodynamic lens can be used to confirm particle presence in the beam. Ion optics can be employed to select and focus particles into said electrostatic trap. The mass to charge ratio m/z ratio of the particle in the trap can be determined by the processor from its oscillation frequency, f, using the following relationship:

$$m/z = \frac{c}{f^2} \quad (1)$$

wherein the calibration factor C is dependent on trapping potentials and the kinetic energy-per-charge of the trapped particle. The processor can calculate the velocity of the particle in the trap by measuring the temporal width of the output pulses ($t_{pulse\ width}$) from an image charge detector ICD2 of length $L_{ICD2}$:

$$v_{particle} = \frac{t_{pulse\ width}}{L_{ICD_2}} \quad (2)$$

The device can include a linear accelerator for accelerating a trapped particle toward a target. The trapped particle is released into the linear accelerator at a time calculated to achieve a predetermined velocity and timing via subsequent acceleration or deceleration of the particle in the linear accelerator given its calculated mass-to-charge ratio. The processor can calculate the accelerated velocity of the particle and determine if the particle has rebounded from the collision target, and can calculate the rebound velocity of the particle from the rebounding peak width. The collision target can be a freestanding film that is imaged upon particle impact for damage or destruction. The target's module can have integrated sensors such as a multichannel plate detector that permits particle fragmentation to be imaged using a phosphor screen an external camera.

A preferred method can determine the mass to charge ratio of aerosol particles, dusts, and other microparticles and/or nanoparticles. The method creates a focused stream of micro or nanoparticles, and traps a single particle at a time from the focused stream in an electrostatic trap. While the single particle is trapped, the amplitude and frequency of the oscillation of the trapped particle is sensed. The mass to charge ratio of the single particle is determined from the amplitude and frequency of oscillation. In preferred methods, the temperature and/or phase of the single particle is altered. This can include heating, cooling or freezing of the particle. The particle can also be released into a linear accelerator at a time calculated to achieve a predetermined velocity and timing via subsequent acceleration or deceleration of the single particle in the linear accelerator given its calculated mass-to-charge ratio. The collision of the single particle emitted from the linear accelerator into a target can be monitored.

BRIEF DESCRIPTION OF THE DRAWINGS

FIG. 8 is experimental data showing a 2D histogram of peak height of 990 nm PSLs arriving at ICD-QD2, plotted against QD potential. ICD-QD2 is not directly calibrated, but the calibration factor can be inferred by reference to another detector. The average number of charges on a 990 nm PSL as measured by ICD2 for particles selected with the QD set to 400 V is 17000, as measured by ICD2. This corresponds to a peak height of 0.45 V on this detector, so the Rayleigh limit of 26500 charges would correspond to about 0.7 V (as shown by the dashed red line). The large number of peaks with amplitudes of <0.2 V are due to particles that have hit the detector pickup instead of passing all the way through;

DETAILED DESCRIPTION OF THE PREFERRED EMBODIMENTS

Figure 1:
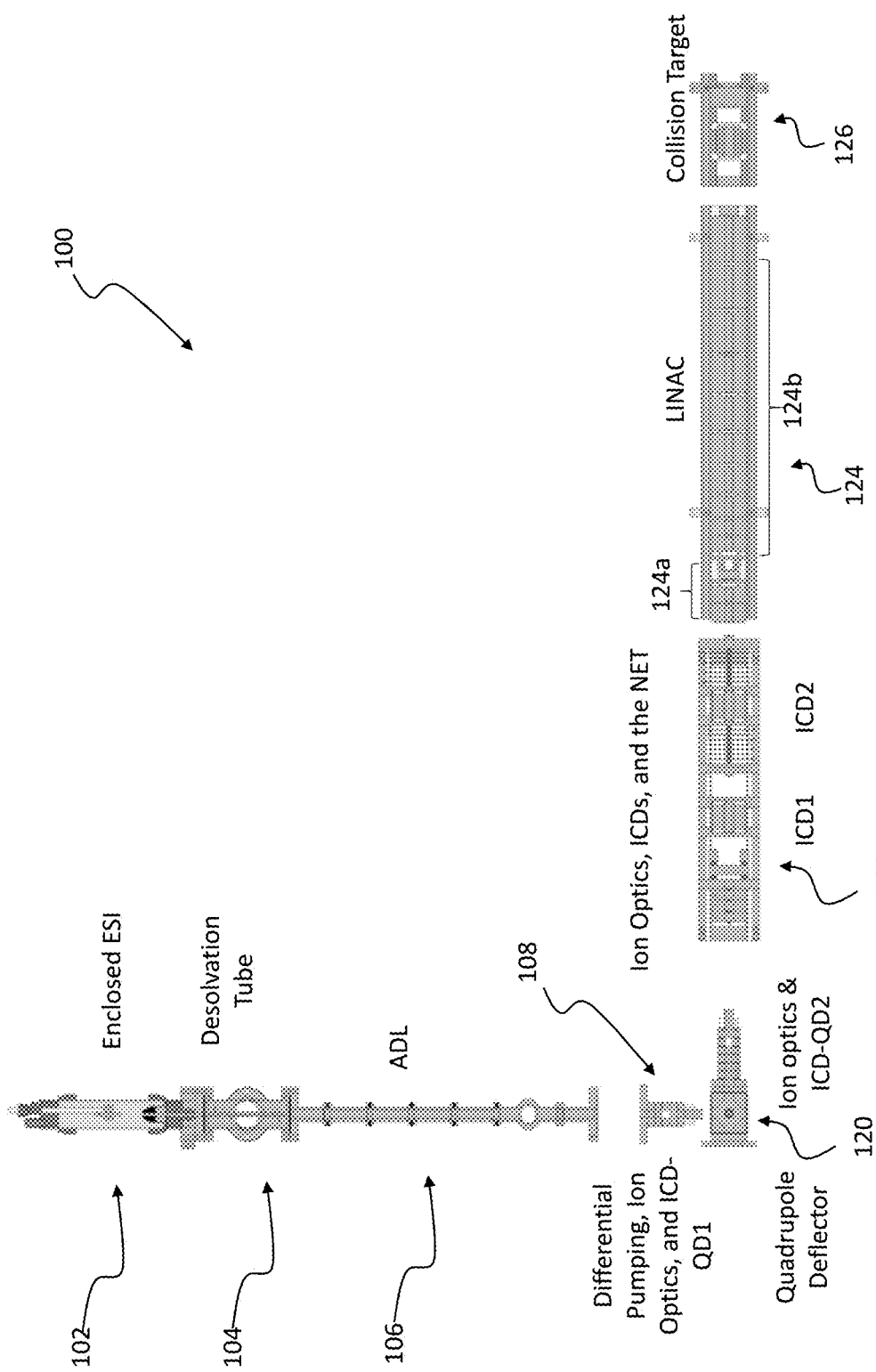
FIG. 1 is a schematic exploded view of a spectrometer in accordance with a preferred embodiment of the invention.

Preferred embodiments of the invention include a spectrometer and spectrometry methods that measure the mass and charge of single charged nanoparticles, accelerate/decelerate the particles to a desired final velocity measure the impact, fragmentation and deposition of the particles interacting with desired substrates. A preferred embodiment spectrometer can accelerate/decelerate a wide size range of nanoparticles, and provides new methods for measurements of fundamental aspects of particle-surface interactions that play a critical role in a wide range of complex ambient and industrial environments. An important aspect of the preferred embodiment and the invention generally is the ability to accelerate or decelerate single charged particles of a known mass to specific final velocities, as determined in real time during the analysis. Prior accelerators have been able to accelerate particles, but not with the single-particle accuracy in real time provided by spectrometers and spectrometry methods of the invention.

Preferred spectrometry methods of the invention provide a modification of the Kiefer & Jerrold single-molecule mass spectrometry approach, applying a charge-pickup electrode in an electrostatic fast-ion beam trap to monitor the ion density oscillating in the trap and carry out Fourier-transform (FT) mass spectrometry on ensembles of molecular ions. Ring S, Pedersen H B, Heber O, Rappaport M L, Witte P D, Bhushan K G, et al., "Fourier transform time-of-flight mass spectrometry in an electrostatic ion beam trap," Anal Chem. 2000; 72:4041-6; Johnson C J, Shen B B, Poad B L J, Continetti R E. Photoelectron-photofragment coincidence spectroscopy in a cryogenically cooled electrostatic ion beam trap. Rev Sci Instrum. 2011; 82:105105. In preferred methods of the invention, the m/z ratio of a single particle provides the information required to accelerate or decelerate that particle for analysis of particle impact. In a preferred device of the invention, the CDMS determines the m/z ratio for each particle in real time, providing the information required to accelerate or decelerate single particles over a wide range of m/z by generating the appropriate acceleration/deceleration pulsed waveform for a linear accelerator (LINAC) structure composed of a series of cylindrical electrostatic elements. Acceleration of ion ensembles is not hindered by space charge limitations since the effect of space charge is progressively reduced as the particles accelerate. Deceleration of ion ensembles does become problematic as a result of increasing space charge, and that is a benefit of working with single charged nanoparticles where this limitation is not present, which benefit is enabled by devices and methods of the invention Preferred embodiments provide a versatile nanoparticle mass spectrometer/accelerator/decelerator. Experiments have demonstrated that an example experimental spectrometer employing polystyrene latex spheres can provide collision inelasticity on silicon wafers by determination of incident and scattered velocities in measurements of the coefficient of restitution.

A preferred embodiment is a spectrometer device. The device includes a particle ion source coupled with a linear electrostatic trap configured as an image charge detection (ICD) mass spectrometer allows determination of the mass-to-charge ratio and the absolute charge and mass of single particles. The particle ion source can be a nanoparticle ion source, and the system can determine the mass-to-charge ratio and the absolute charge and mass of single nanoparticles. A multi-stage linear accelerator/decelerator (an example embodiment had nine stages) is used to fix the final velocity of the nanoparticles. A data acquisition system uses a transient digitizer interfaced to a field-programmable gate array module that allows real time calculation of m/z and determination of the pulse sequence for the linear accelerator/decelerator.

Example experiments have demonstrated the coefficient of restitution for polystyrene latex spheres (PSLs) impacting on silicon measured using ICD techniques. Electrospray ionization of a colloidal suspension of PSL spheres of 510 and 990 nm has been used to demonstrate acceleration and deceleration of charged nanoparticles and the resolution of the example experimental apparatus. Measurements of the coefficient of restitution for PSLs on silicon over the range 10-400 m/s are consistent with previous studies.

Preferred embodiments provide a versatile nanoparticle mass spectrometer/accelerator/decelerator, referred to as the Aerosol Impact Spectrometer (AIS), which has been demonstrated via experiments with polystyrene latex (PSL) spheres, including studies of collision inelasticity on silicon wafers by determination of incident and scattered velocities in measurements of the coefficient of restitution Example experiments have demonstrated the measuring of thin film durability under repeated particle impact. Electrospray ionization of both 990 nm PSL spheres and 500 nm metallic tin powder have been used to demonstrate controlled acceleration and gating of particles prior to impact on free-standing thin film targets. Measurements of different film thickness and material durability have been performed with both particle species.

Example experiments have demonstrated the measurement of particle impact fragmentation distributions using a multichannel plate with phosphor screen detector. Electrospray ionization of both 500 nm metallic tin powder and large solvent droplets have been used to demonstrate acceleration above 700 m/s and particle impact directly onto the face of a multichannel plate. Post impact fragments have been imaged with a phosphor screen and CCD camera.

Preferred embodiment methods and devices irradiated a particle with a laser chosen to heat or otherwise excite the nanoparticle while the particle is held in an oscillatory trajectory in the NET. A particular advantage of such heating or other excitation is an ability to control the phase (solid vs. liquid) of the nanoparticles, and examine the effect of this particle phase on the particle-substrate interactions following acceleration/deceleration.

Those knowledgeable in the art will appreciate that embodiments of the present invention included detection and data acquisition methods and control methods that lend themselves well to practice in the form of computer program products. Accordingly, it will be appreciated that embodiments of the present invention may comprise computer program products comprising computer executable instructions stored on a non-transitory computer readable medium that, when executed, cause a computer to undertake methods according to the present invention, or a computer configured to carry out such methods. The executable instructions may comprise computer program language instructions that have been compiled into a machine-readable format. The non-transitory computer-readable medium may comprise, by way of example, a magnetic, optical, signal-based, and/or circuitry medium useful for storing data. The instructions may be downloaded entirely or in part from a networked computer. Also, it will be appreciated that the term "computer" as used herein is intended to broadly refer to any machine capable of reading and executing recorded instructions. It will also be understood that results of methods of the present invention may be displayed on one or more monitors or displays (e.g., as text, graphics, charts, code, etc.), printed on suitable media, stored in appropriate memory or storage, etc.

A preferred embodiment spectrometer 100 is shown in FIG. 1. The spectrometer includes an enclosed electrospray ionization source 102. The electrospray ionization (ESI) ion source 102 and beam line including a desolvation tube 104 and an aerodynamics lens (ADL) 16 that focuses into a differential pumping ion optics section 108 and a quadrapole deflector QD 120, which directs an energy selected beam into a nanoparticle electrostatic trap (NET) 122 and a linear ion accelerator (LINAC) 124 that accelerates the energy selected beam into a collision target module 126 having a target and sensors. The target 126 module can have integrated sensors such a collision target that comprises a multichannel plate detector permitting particle fragmentation to be imaged using a phosphor screen an external camera. An alternative sensor is a conductive surface connected to a charge-sensitive amplifier for measuring the impact charge and charge transfer to the target. The NET 122 of a preferred experimental embodiment, and system in general, can handle a wide range of nano and microparticle sizes, with an example range being from ~50 μm to ~5 μm. More specifically, the quadrupole deflector (QD) 120 provides an energy selected beam of single nanoparticles for analysis in the nanoparticle electrostatic trap (NET) 122. The QD 120 can be operated over a wide energy range, selecting different particle distributions as determined by the size, charge and ESI expansion conditions. The FIG. 1 QD 120 is configured to redirect the energy selected beam orthogonally, where particles of the selected mass range are redirected to the axis of the NET 122 and other particles are not redirected. The orthogonal arrangement is not critical, and other deflectors can selectively transmit particles of a predetermined mass at various angles, including co-axially with the NET 122. In a co-axial arrangement, for example, the particles of interest would not be deflected and the particles not of interest would be deflected. Artisans will appreciate various techniques for provide a stream of size/mass selected particles to the NET 122. Various targets can be used for the collision target, e.g., silicon, diamond, molybdenum, stainless steel, silicon nitride, and molybdenum disilicide, among others. The goal of testing will determine the type of particle accelerated and the type of target impacted, as well as the phase of the particle accelerated. Example targets can include semiconductor layers or substrates to evaluate the effects that particle contamination can have during fabrication. The ESI 102 can also provide biological cells and large biological molecules and complexes in the gas phase as particles to be accelerated. The phase of particles in the NET 122 can be controlled, the particles can be heated, such as by laser energy, or cooled including to a frozen state while in the NET 122 (via refrigeration of the NET 122). In one variation, the chamber for the NET 122 includes a commercial Stirling cooler or another type of closed-cycle helium refrigerator to cool the NET 122 and freeze the particles while trapped in the NET 122. In addition to studying the particle after impact, the target can be removed after impact and tested, such as for erosion. In one variation, a sample holder for the target is rotatable, which permits grazing incidence measurements. The arrangement and control of the components in the FIG. 1 system enables determination, in real time and for a single particle, the mass-to-charge ratio, the charge, and thus the mass while the particle is trapped in the NET 122, and also the determination of the acceleration/deceleration waveform on the LINAC 124 to bring the particle to the desired velocity for impact on the collision target. The size of the particles that can be handled in the FIG. 1 devices is wide in range. An example experimental device in according with FIG. 1 required about 500 elementary charges, which sets the minimum size particle to ~50 μm. The experimental device also can handle particles up to ~5 μm.

Charged particles are formed by electrospray ionization in the ESI 102 and transferred into a low vacuum through a 150-μm Pt electron microscope aperture. The desolvation tube 104 heats and dries the particles before they enter the ADL 106, which collimates and focuses the particle beam. The particle beam passes through two stages of differential pumping to reduce the ambient pressure prior to mass analysis and acceleration/deceleration in pumping section 108 and enters a chamber that houses the electrostatic quadrupole deflector 120. The QD 120 selectively turns particles, based on their kinetic energy per charge, 90° and into the next chamber that contains the nanoparticle electrostatic trap 124. The NET 122 is a linear electrostatic trap configured as an image charge mass spectrometer. The NET can be constructed as first described by Zajfman and colleagues on ion ensembles (Zajfman D, Heber O, Vejby-Christensen L, Ben-Itzhak I, Rappaport M, Fishman R, et al. Electrostatic bottle for long-time storage of fast ion beams. Physical Review A. 1997; 55:R1577-R1580; Dahan M, Fishman R, Heber O, Rappaport M, Altstein N, Zajfman D, et al. A new type of electrostatic ion trap for storage of fast ion beams. Rev Sci Instrum. 1998; 69:76-83), and in a single-particle application by Benner (Benner W H. A gated electrostatic ion trap to repetitiously measure the charge and m/z of large electrospray ions. Anal Chem. 1997; 69:4162-8). The NET 122 is gated to trap one particle at a time, before measuring the mass-to-charge ratio and the absolute charge of the particle. These particles can be trapped in the NET 122 with an efficiency ~70% for periods in excess of 5 seconds with a distribution of oscillation frequencies in the several hundred Hertz range. A Labview-based data acquisition code uses the m/z data to calculate the required switching times for the LINAC 124 to accelerate the particle up to the required velocity. The particle is then released from the trap into the LINAC for acceleration to the determined velocity.

An example LINAC 124 is a 40 element LINAC with 25 kV acceleration per element (using commercially available 30 kV fast switches) which permits acceleration across a potential difference of 1 megavolt. For aerosols >100 nm, many charges (100-1000) can be accommodated, allowing impact velocities, depending on charge and mass, as high as 8 km/sec as shown in Table 1 below. These velocities represent upper limits for each mass and charge:

| Particle size (nm) | Mass (amu) | $V_{final}$ (km/sec) q = 1 | $V_{final}$ (km/sec) q = 10 | $V_{final}$ (km/sec) q = 100 | $V_{final}$ (km/sec) q = 1000 |
|---|---|---|---|---|---|
| 50 | $3 \times 10^7$ | 2.5 | 8 | 25 | |
| 100 | $2.7 \times 10^8$ | 0.8 | 2.6 | 8.4 | |
| 250 | $4.2 \times 10^9$ | 0.21 | 0.68 | 2.2 | 6.8 |
| 500 | $3.4 \times 10^{10}$ | 0.08 | 0.24 | 0.76 | 2.4 |
| 1000 | $2.3 \times 10^{11}$ | 0.03 | 0.09 | 0.29 | 0.92 |

Table 1 shows, assuming cubic carbon nanoparticles, mass and terminal velocities upon acceleration through 1 megavolt in the LINAC 124 for varying numbers of charges. Reduction of the terminal velocity out of the accelerator 124 is accomplished by reducing the acceleration potential. In practice, the pulse duration and starting time vary as the square root of the mass. Acceleration will be triggered using the signal from the image charge detection assembly. For relatively narrow mass distributions it is unnecessary to adjust in real-time. A final charge pickup electrode structure at the exit of the LINAC 124 can be used to provide the timing signal for initiating pulsed laser irradiation of the particle (LDI) or VUV photoionization of secondary neutral products, as well as triggering the mass spectrometer and photomultiplier data acquisition system. The acceleration in the LINAC 124 can also be controlled to achieve a specific goal for impact with the target 126, for example, a predetermined range of velocity can be selected to cause the particle to split upon impact, vaporize upon impact, rebound upon impact, etc. The FIG. 1 can operate in real time to achieve any of those goals while accelerating a predetermined single nano or microparticle in a predetermined phase, e.g. heated or frozen.

In an experimental apparatus, the ESI 102 consisted of a 360 μm O.D., 75 μm I.D. fused silica capillary mounted on an isolated aluminum block, which is held at approximately +4-6 kV. The experiments studied positively charged particles, but the spectrometer 100 in FIG. 1 can also be run to study negatively charged particles by changing the polarity of all of the electrostatic potentials. The tip of the capillary is positioned ~10 mm in front of a 150 μm aperture and is enclosed within a glass tube. The aperture is mounted on a 6.4 mm OD, 3.86 mm ID stainless steel tube that passes through a ¼" Ultra-Torr fitting into the instrument. The portion of this tube that extends out of the vacuum chamber is surrounded by an enclosure, through which nitrogen, heated to ~85° C., flows. The heated nitrogen helps to desolvate the particles, and also acts as a curtain gas. 510 nm (Polyscience #07307) and 990 nm (Polyscience #07310)

PSL spheres were suspended in 1:1 mixtures of 25 mM aqueous ammonium acetate and methanol then delivered to the electrospray tip by a syringe pump operating at a rate of 0.26 mL/h. The final number densities were $3.0 \times 10^9$ particles per mL for the 510 nm PSL suspension, and $4.1 \times 10^8$ particles per mL for the 990 nm suspension. After entering the vacuum chamber, the particles pass through a 120 mm long, 4.5 mm I.D. stainless steel tube, which is heated to ~185° C. to completely desolvate the particles, and to evaporate charged solvent droplets.

After exiting the heater tube, the particles enter the ADL 106, which aerodynamically focuses and collimates the beam of particles. The ADL 106 is structured consistently with the principles described by Liu et al. described by Daly et al. and Liu et al. See Liu P, Ziemann P J, Kittelson D B., "Generating particle beams of controlled dimensions and divergence: I. Theory of particle motion in aerodynamic lenses and nozzle expansions," Aerosol Sci Tech. 1995; 22:293-313. In the experimental apparatus, the aerodynamic lens consists of 5 apertures separated by 59 mm long, 12.1 mm I.D. spacers. The diameters of the apertures are 5.9, 5.3, 4.6, 3.4 and 3.1 mm. The section after the $5^{th}$ aperture is connected to a mechanical vacuum pump. The pressure at the start of the ADL is 2.6 Torr, and the pressure in the pumped region is typically in the range of 0.5-1 Torr. The precise pressure after the ADL 106 is adjusted, by throttling the vacuum pump, in order to maximize transmission of particles in a specific size range. Calculations consisting with those described by Wang and McMurry (Wang X, McMurry P H. A design tool for aerodynamic lens systems. Aerosol Sci Tech. 2006; 40:320-34) indicate that the ADL in the experimental apparatus should transmit over 95% of particles in the range of 75-1200 nm.

Following the ADL 106, the particles pass through a 3.1 mm diameter aperture into the first differential pumping stage, which is connected to a Roots blower backed by a rotary mechanical pump. This pumping stage also contains an image charge detector tube (ICD) to confirm transmission of particles through the aerodynamic lens. A 5 mm aperture leads to the second differential pumping stage, pumped by a Pfeiffer TMH 064 turbomolecular pump. A 3.2 mm aperture separates the second differential pumping stage from the quadrupole deflector chamber, which is pumped by an Osaka TG240 turbomolecular pump. The quadrupole deflector chamber is pumped to a vacuum of $3 \times 10^{-5}$ Torr.

The QD assembly 20 is in the center of the chamber and consists of 4 parallel, quarter-cylinder stainless steel rods (19 mm radius). The rods are mounted on ⅛" precision ground glass spheres that locate the rods such that their curved faces are tangential to an inscribed circle of 33.7 mm diameter. Positive and negative potentials are applied to opposing pairs of rods, resulting in an electrostatic field that will turn particles that have kinetic energy, in eV per charge, equivalent to the potential applied to the rods. Particles with excess kinetic energy will overshoot the bend, whereas particles with less kinetic energy will impact the electrode on the inside of the curve.

There are two sets of ion optics in the chamber with the QD 120, each comprised of an einzel lens, an x-y deflector and an image charge detector (ICD), modeled after the image charge detector presented by Fuerstenau and Benner (Fuerstenau S D, Benner W H. Molecular weight determination of megadalton DNA electrospray ions using charge detection time-of-flight mass spectrometry. Rap Comm Mass Spec. 1995; 9:1528-38). One image charge detector ICD-QD1 is positioned before the entrance to the QD 120, the other image charge detector ICD-QD2 after the exit from the QD 120. These ion optics serve to focus the selected particles and direct them to the next chamber, which contains the NET 122 and LINAC 124. The first ICD (ICD-QD1) is used to confirm transmission of particles through the ADL. The second ICD (ICD-QD2) is used to determine the optimal deflector potential to direct the particle beam towards the next chamber.

Figure 2:
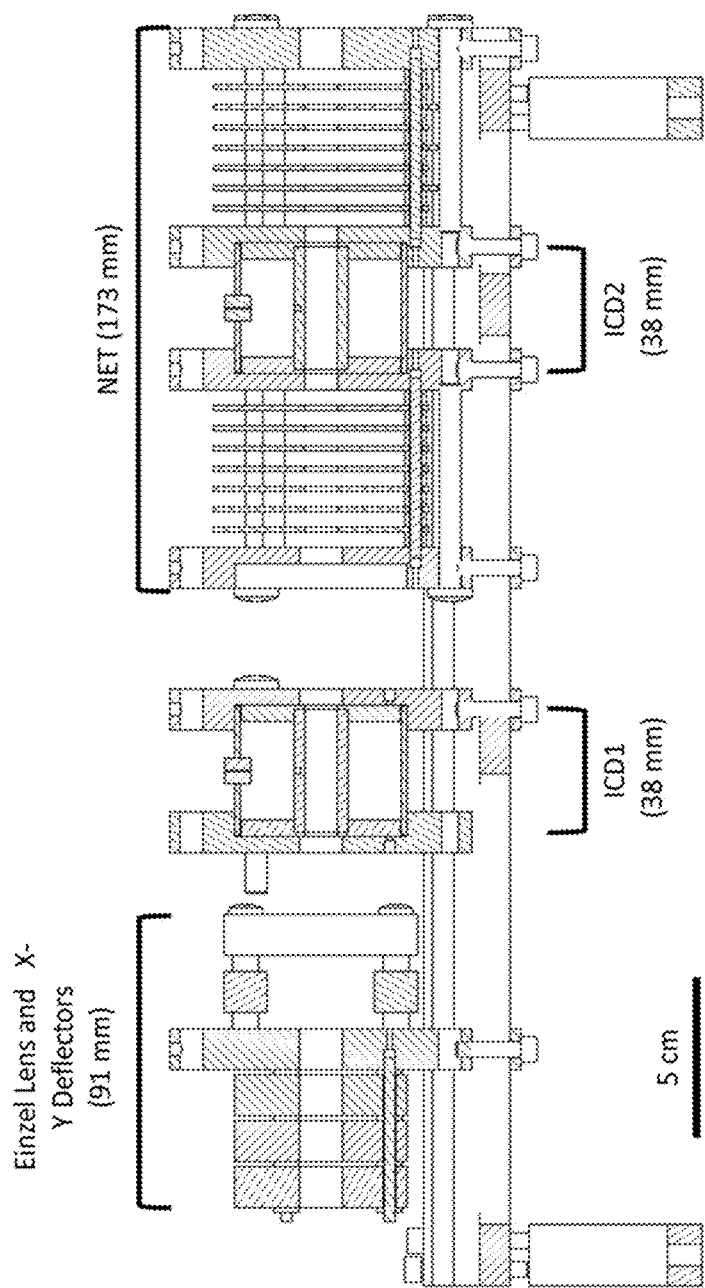
FIG. 2 is a side schematic view of a preferred nanoparticle electrostatic trap of the FIG. 1 spectrometer.

After the QD 120, the energy-selected particles are passed into the NET chamber 122 through another set of electrostatic optics (einzel lens and x-y deflectors) mounted on an isolated rail system, which is shown in FIG. 2. This assembly is mounted in a vacuum chamber that is pumped by another Osaka TG 240turbomolecular pump and achieves vacuum of $10^{-6}$ Torr. An image charge detector ICD1 is located directly after the optics stack to track transmission of particles into the NET chamber 122. ICD1 connects directly to the junction field-effect transistor (JFET) input of an Amptek A250 charge-sensitive amplifier circuit mounted in vacuum on the grounding plates shielding the detector. Output from the ICD1 circuit passes to a feedthrough where it can be monitored externally.

Figure 3:
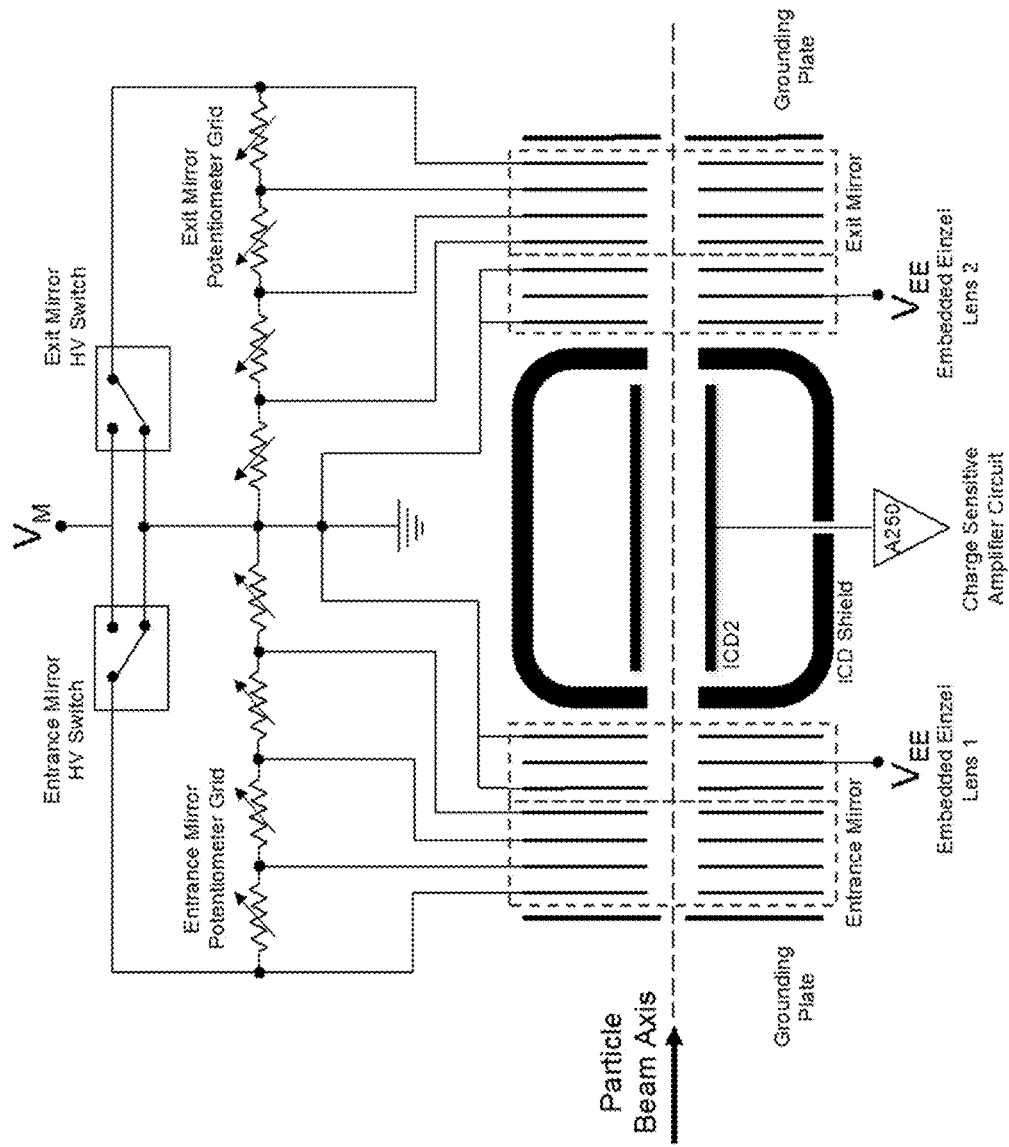
FIG. 3 is a schematic diagram of the lens and circuits of the nanoparticle electrostatic trap of the FIG. 1 spectrometer.
Figure 4:
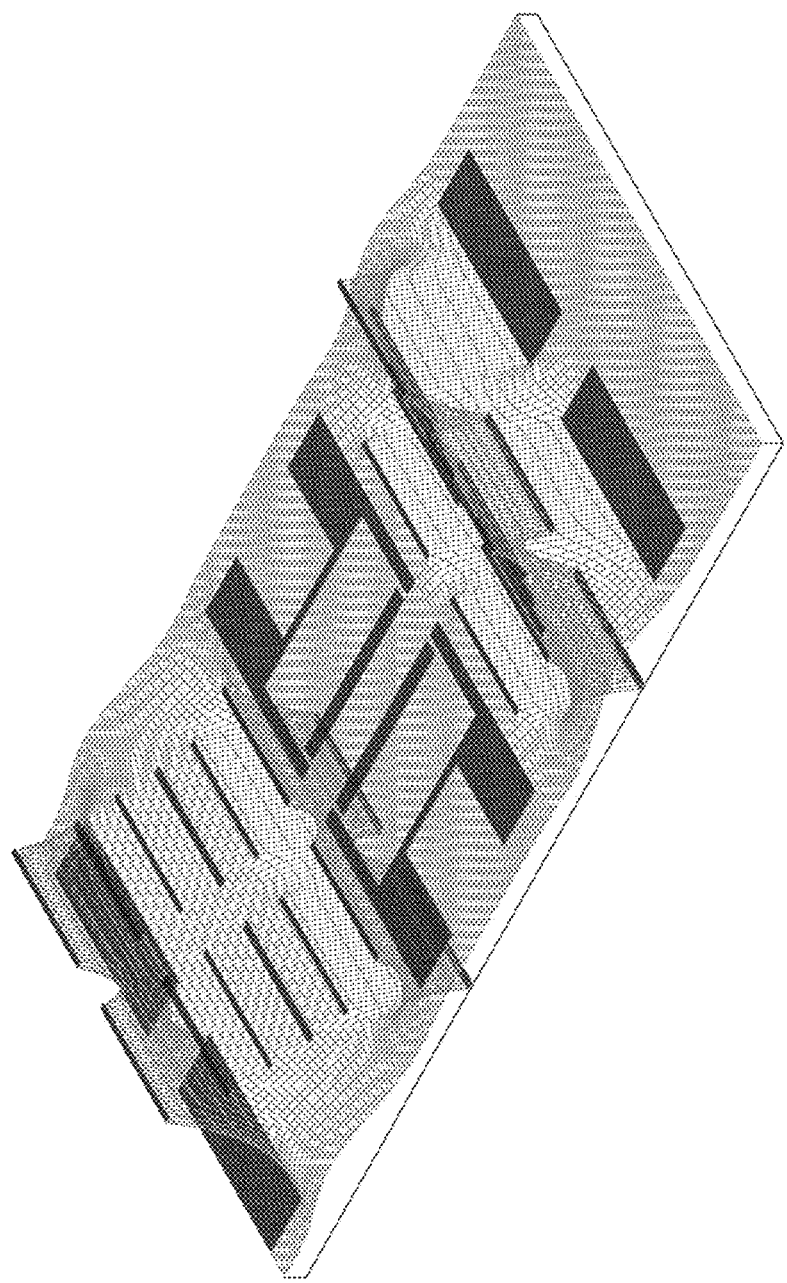
FIG. 4 is SIMION (8.1) representation of the potentials in the nanoparticle electrostatic trap of the FIG. 1 spectrometer.

After passing through ICD-QD2, particles are transmitted into the NET 122. The design of the NET 122 was modeled after the ion trap of Benner (Benner W H. A gated electrostatic ion trap to repetitiously measure the charge and m/z of large electrospray ions. Anal Chem. 1997; 69:4162-8). Details of the NET 122 are shown in FIG. 3. Two electrostatic mirrors each composed of four individual elements connected by a network of external potentiometers establish the fields that trap the charged particles. The mirror elements have an outer diameter of 63.5 mm, a beam-line inner diameter of 9.7 mm and a thickness of 1.5 mm Each mirror stack incorporates an additional three elements that act as an intracavity einzel lens to refocus trapped particles. The NET 22 has an ICD (ICD2) mounted in the field-free region centered between the two, seven-element mirror stacks. ICD2 is a 38.1 mm long tube with an outer diameter of 15.9 mm and an inner diameter of 9.5 mm. The tube is isolated with PEEK insulators that mount on the final grounded einzel element of each mirror stack. The elements in each mirror stack are spaced by 4.8 mm nylon spacers mounted on alumina rods that hold the seven elements in place. The entire assembly is enclosed by two grounded plates and mounted on the isolated rail system with a total length of 173 mm Each mirror stack is wired to a multipin feedthrough that connects to an external network of potentiometers. Each network is set up as a multistep voltage divider that controls the potential and field shape of each mirror stack independent of the other. The potentiometer grids are wired to two home-built high voltage (4 kV) MOSFET switches that control the mirror potentials. Potentials used on the NET mirrors are the same polarity as the charge of the particles being trapped. The intracavity-einzel lens can be operated in either polarity to establish a stable potential for trapping. SIMION 8.1.1 was used to generate a model of the field used in this experiment for the NET 122. The model is shown in FIG. 4. ICD2 is wired directly to the junction field-effect transistor (JFET) input of an Amptek A250 charge sensitive amplifier circuit. This circuit is mounted in a shielded box directly above the assembly, and the output is connected with shielded coaxial cable to a coaxial feedthrough.

Figure 5A:
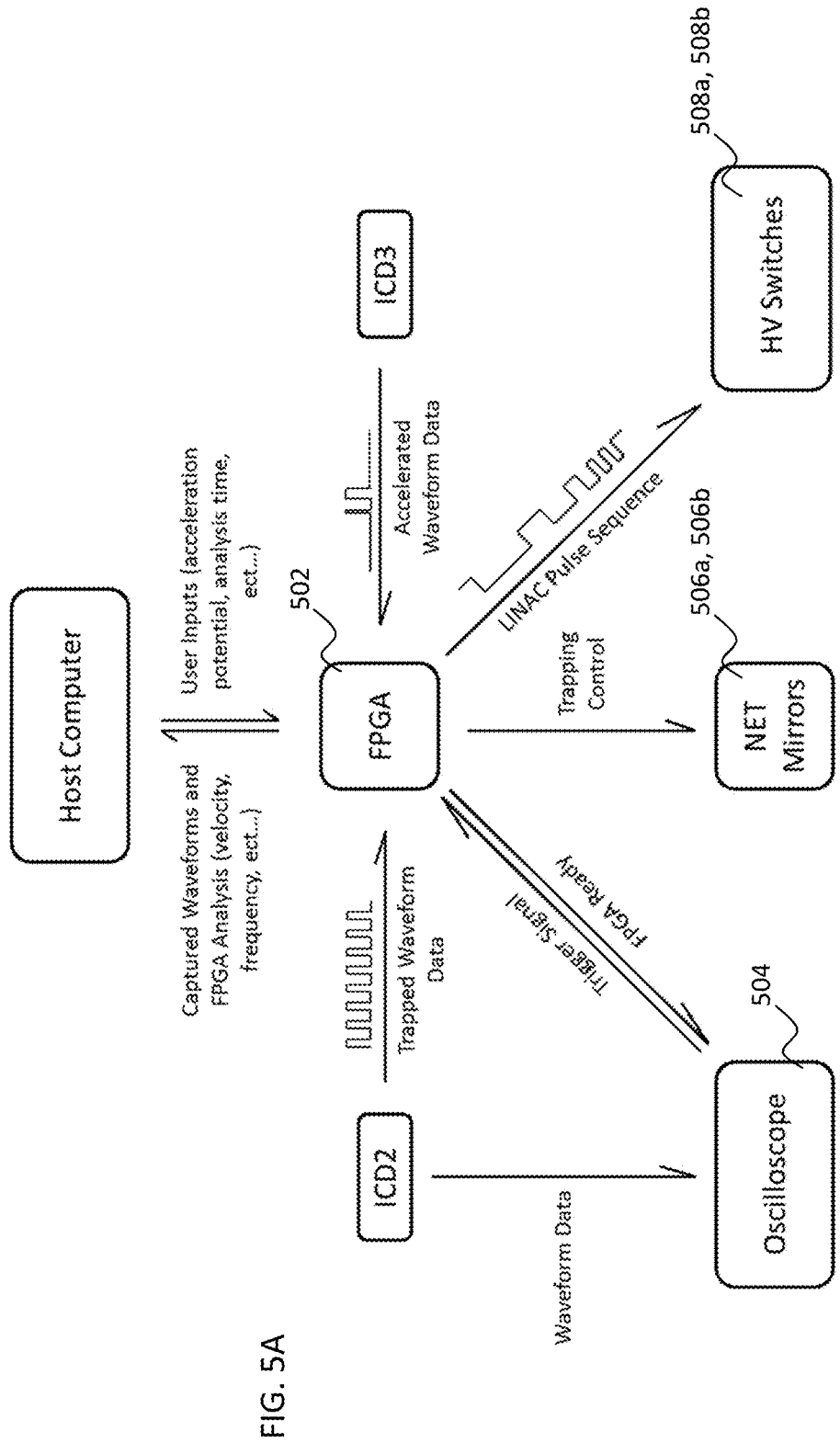
FIGS. 5A and 5B are schematic diagrams of the control system of the FIG. 1 spectrometer.
Figure 5B:
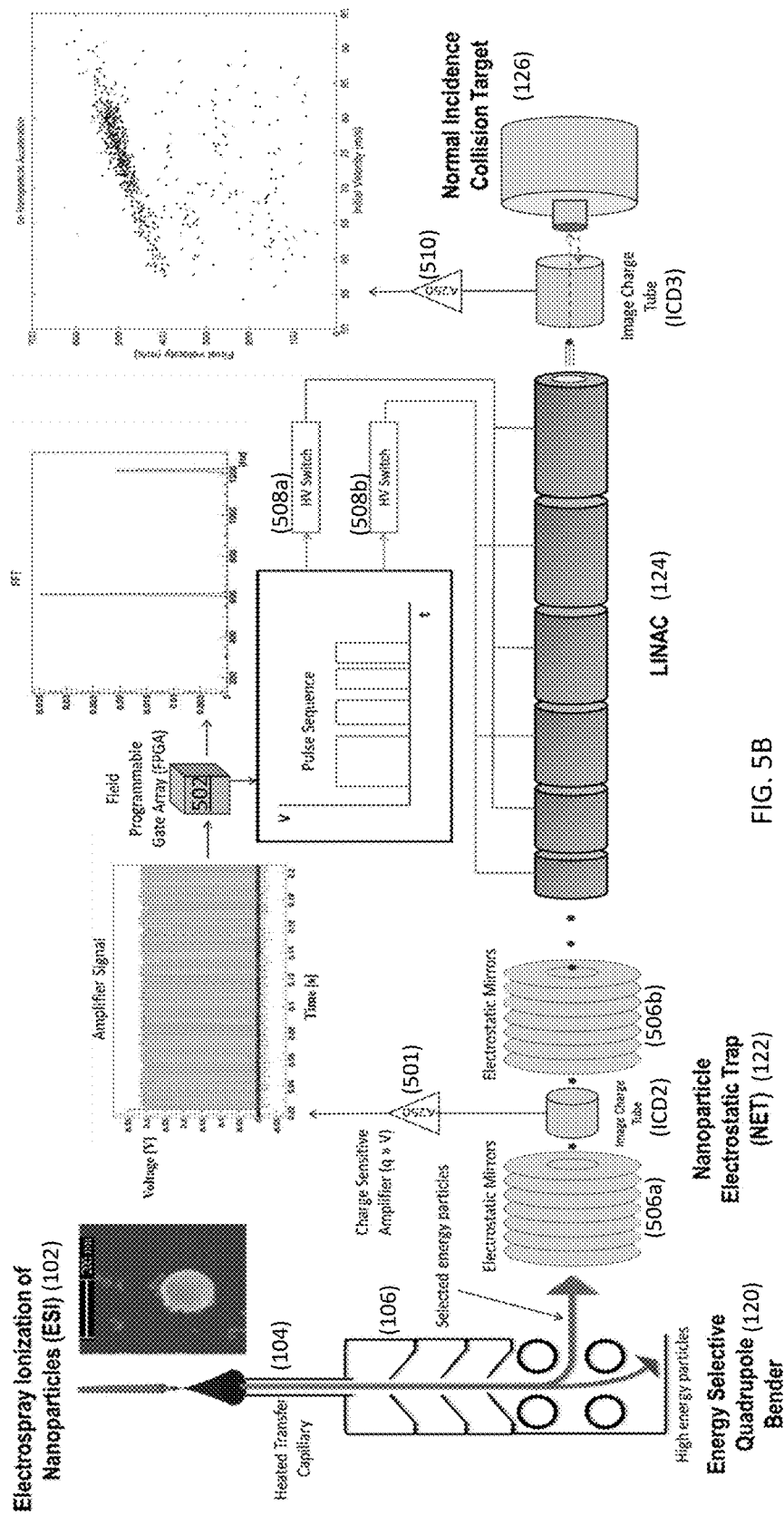

FIGS. 5A and 5B illustrates the signal transfer for the control system of the FIG. 1 spectrometer. The signal from the NET 122's ICD2 is connected to an amplifier 501 for baseline subtraction and signal gain. The output of this amplifier 501 is connected to a field programmable gate array 502 (FPGA) (National Instruments PXI-7952R) with a high-speed digitizer front end (National Instruments NI 5731) and an oscilloscope 504 (Tektronix DPO 3034). The FGPA 502 provides control signals to the mirrors 506 in the NET 122, and also provides LINAC pulse signals to high voltage (HV) switches 508a and 508b in the LINAC 124, which control alternating sections of the LINAC 124 for particle acceleration. The overall gain of the amplifier 501 is determined by applying a 5 mV trapezoidal waveform, with rise and fall times similar to those of the waveforms induced by the oscillating particles, through a 1.5 pF capacitor attached directly to the ICD2 pickup. The capacitor converts the known voltage to a known charge, and the amplified response to the known input provides the overall gain calibration factor. The experimental apparatus has successfully detected particles with as low as 1000 charges. Based on variation in the response to the calibration input signal, the 1 standard deviation uncertainty on the charge measurement is roughly 100 charges. The initial state of the NET 122 has the entrance mirrors 506a potential lowered, and the exit mirrors 506b potential raised. When a particle passes through ICD2 in the NET 122, the output pulse from the charge-sensitive amplifier triggers closing of the entrance mirror 506a. With both mirror sets 506a, 506b raised the charged particle oscillates in the trap producing a regular signal from ICD2 with a measurable amplitude and frequency. This signal is captured by the FPGA digitizer 502 and analyzed by a LabView code while the particle is still trapped. The m/z ratio of the particle in the trap is determined from its oscillation frequency, f, using the following relationship:

$$m/z = \frac{c}{f^2} \quad (1)$$

The calibration factor C is dependent on the trapping potentials of the NET 122 and the kinetic energy-per-charge of the trapped particle. This factor is calculated using a SIMION simulation with these parameters. See, Dahl D A. SIMION for the personal computer in reflection. Int J Mass Spec. 2000; 200:3-25. In addition to frequency, the FPGA 502 calculates the velocity of the particle in the NET 122 by measuring the temporal width of the output pulses ($t_{pulse\ width}$) from ICD2 of length $L_{ICD2}$:

$$v_{particle} = \frac{t_{pulse\ width}}{L_{ICD_2}} \quad (2)$$

This data is measured and calculated on the fly for each particle and is used to create the timing sequence used by the HV switches 506a, 506b of the LINAC 124 for acceleration/deceleration.

Directly after the NET 122 there is a pair of x-y deflectors 124a (see FIG. 1), mounted on a second isolated rail system in the same chamber. This rail system has the same layout and mounting as the NET 122, and allows the LINAC 124 to be removed from the chamber independently of the NET 122. After the deflectors in the experimental device, ten cylindrical polished stainless steel electrodes 124b (see FIG. 1) are mounted 1.7 mm apart on the remaining length of the rail. The accelerator electrodes all have a 50.8 mm outer diameter, a 10.16 mm inner diameter, and beveled edges. The first four electrodes are all the same length ($L_1$=20.32 mm), with the length of each subsequent element determined by the following relationship:

$$L_n = L_1 * \sqrt{n}; \ n=\{2, 3, 4, \ldots, 9\} \quad (3)$$

The first three electrodes act as a lens with each element connected to external power supplies (two KIKUSUI PMC350-0.2A and one Canberra 3002). The remaining 9 electrodes are wired through two HV feedthroughs (30 kV) with every second element collectively wired to one feedthrough and every other element collectively wired to the other feedthrough. All elements in each set are connected together with copper rods. These two rods are connected to each HV feedthrough with a shielded HV cable. The elements are pulsed with two 30 kV HV switches (Behlke 301-03-GSM).

To calculate the timing used to trigger the two HV switches 508a, 508b, the data acquisition program uses the m/z of the particle and the initial velocity to perform a simulation of the particle travelling through the LINAC. This is accomplished be using a position-dependent electric field equation derived from a SIMION model of the LINAC electrodes. A code steps through time and velocity to calculate the acceleration of the particle under the influence of the electric field:

$$t_x = t_{x-1} + \left(\frac{dx}{v_{x-1}}\right) \text{ and } v_x = v_{x-1} + \left(\frac{E_{x-1}}{m/z} * (t_x - t_{x-1})\right). \quad (4)$$

In equation (4), $t_x$ is the time at position x, $v_x$ is the velocity at position x, $E_x$ is the electric field at position x, and dx is the step size of the calculation, in this case 0.01 mm. This timing calculation is performed while the particle is still trapped in the NET 122. Upon completion of the calculation, timing data is transferred to the FPGA 502. The FPGA then releases the particle from the trap by lowering the exit mirror and triggers the two HV switches 508a, 508b at times required to accelerate/decelerate the particle to a final energy that depends on the number of elements used and the potential applied to each element. An important advantage realized by preferred embodiments of the invention is the ability to trap a single particle in the NET 122, time its entry into the LINAC 124, and generate the appropriate pulse sequence on the LINAC elements to accelerate or decelerate the particle to the desired predetermined final velocity. The values chosen for acceleration or deceleration to a desired predetermined final velocity depend on the target and experiment goal, as discussed above.

Figure 6:
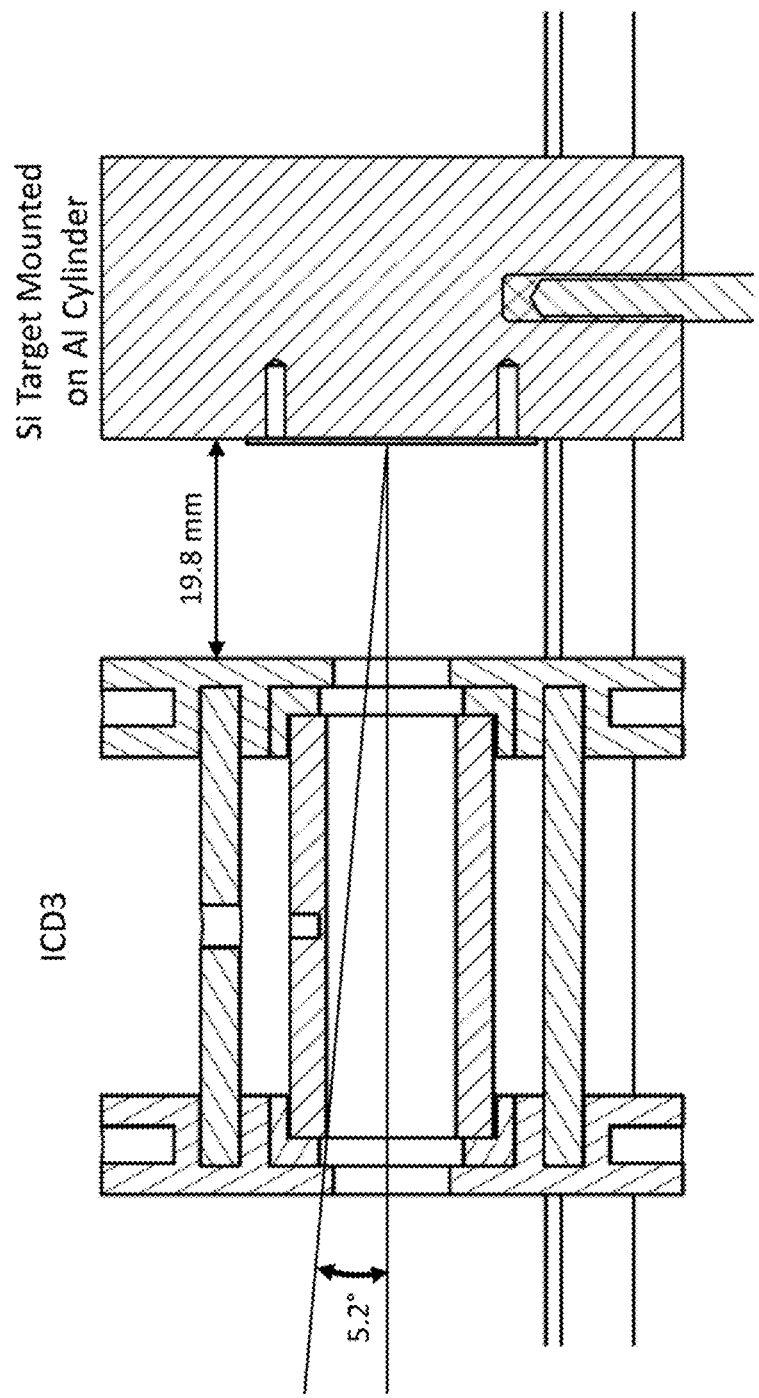
FIG. 6 is a side schematic side view of a collision target of the FIG. 1 spectrometer.

FIG. 6 shows an example collision target and preferred collision target module. After the LINAC 124, another shielded ICD tube (ICD3) is mounted on an isolated rail system of the same design as the NET 122 and LINAC 124 rails. This rail system is in a chamber pumped by an Osaka TG420 to a vacuum of $10^{-7}$ Torr. ICD3 is placed 19.8 mm in front of an aluminum block on which a collision target is mounted. The collision target used an example experiment was a 2.5 cm square piece of p-type silicon (cut from a polished, 6 inch diameter, 600 μm thick boron doped wafer, Ziti Inc.). An Amptek A250 charge sensitive amplifier circuit 510 is located directly above the ICD3 tube, and the output is connected to the FPGA digitizer 502 through a second baseline subtraction and amplification circuit to capture signals from ICD3. In this specific embodiment, the target and ICD3 were positioned such that particles rebounding at a maximum angle of 5.2° from center can be measured by ICD3 for incident and rebounding beam axis velocity. The 5.2° angle was used for convenience. The angular limit can be varied by changing the distance of ICD3 from the target, and varying the length and/or diameter of the ICD3 pickup tube. In another variation, the particles pass through a sample and are detected by a detector after passing through the sample. The angle should be selected to permit detection of the particles, if desired. In some testing, the particle detection upon a rebound might not be of interest, and/or the particle might be split or vaporized. In some testing, the effect on the target can be the primary or sole interest.

After acceleration, the FPGA digitizer 502 captures a waveform from the output of ICD3. The waveform is transferred to the Labview program which calculates the accelerated velocity of the particle. The program also determines if the particle has rebounded from the collision target, and calculates the rebound velocity of the particle from the rebounding peak width. After completing this final acquisition the program saves all information to a data file and resets itself and the FPGA 502 to accept a new particle. The entire run time for each particle in this experiment was approximately ~200 ms.

Figure 7A:
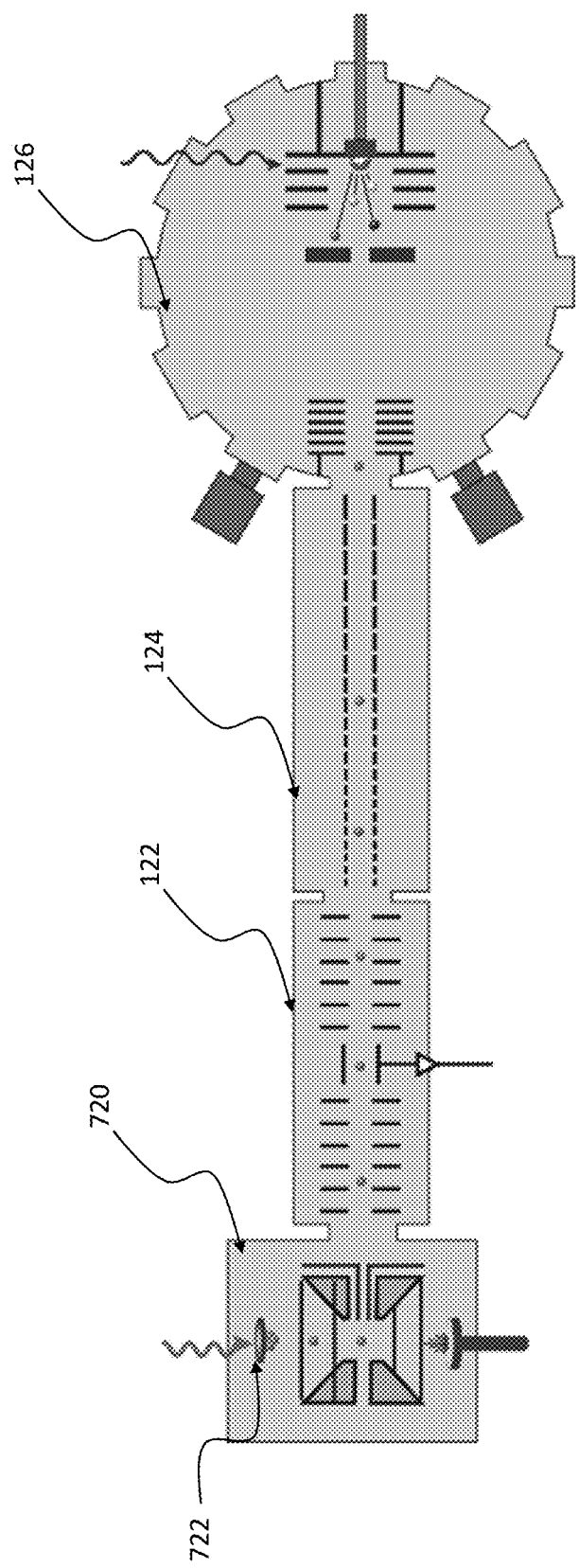
FIG. 7A illustrates a modification of the FIG. 1 spectrometer that includes a quadrupole trap and a laser to excite a nanoparticle before it is trapped in the nanoparticle electrostatic trap.
Figure 7B:
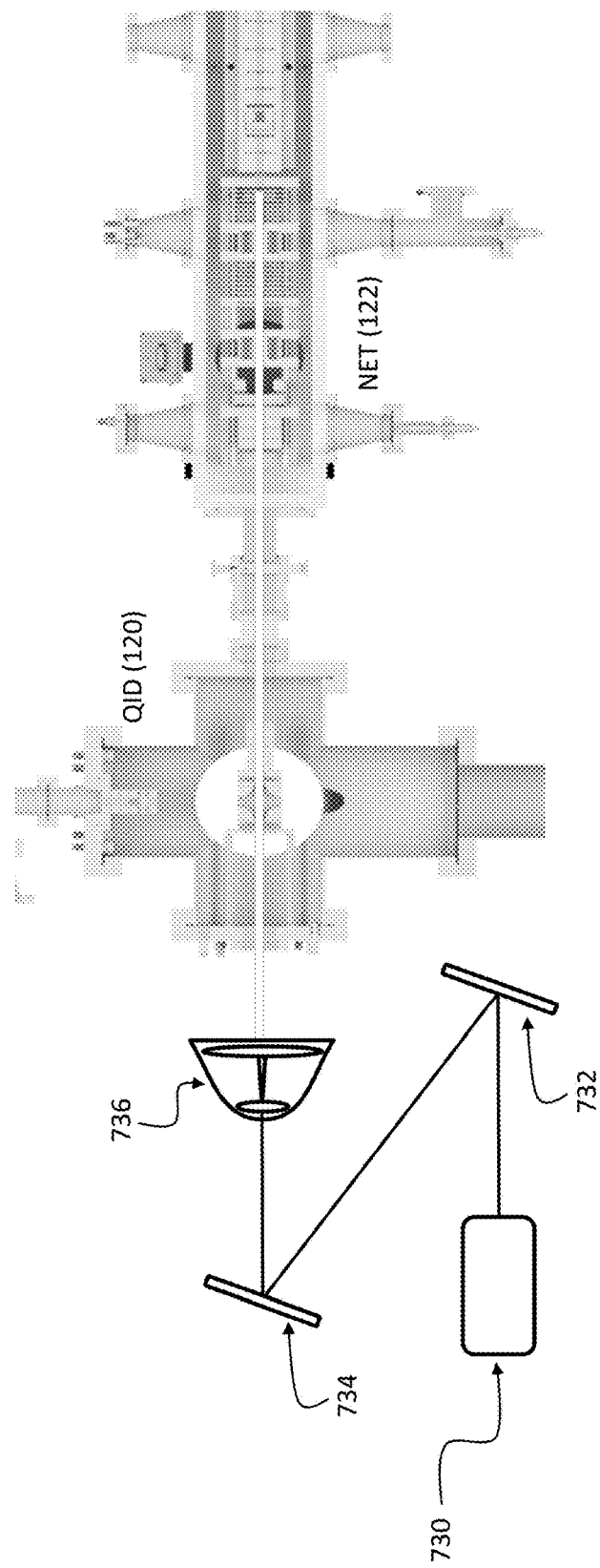
FIG. 7B illustrates a preferred method and variation of the FIG. 1 spectrometer for controlling the phase of a particle in the nanoparticle electrostatic trap.

FIG. 7A illustrates a modification of the FIG. 1 spectrometer that includes a laser and a quadrupole trap/deflector 720 to excite a nanoparticle before it is trapped in the NET 122. The quadrupole trap/deflector 720 includes a substrate coated with particles 722 that allows for either laser-induced acoustic desorption or laser desorption ionization/ablation of a wide range of targets. Laser excitation enables chemical and/or photo aging of trapped particles prior to re-direction of the particles to the NET 122. The laser stimulation can be from a diode laser. Laser desorption ionization (LDI) and vacuum ultraviolet (VUV) ionization lasers can be used in separate experiments to probe isolated aerosols or the secondary neutral products from aerosol impact on the target substrate. Secondary ions from aerosol impact can also be extracted and detected in the collision chamber 126. FIG. 7B shows another modification of the FIG. 1 spectrometer that enables excitation capable of provide a phase change of a particle while it is trapped in the NET 122. A laser 730, e.g. a solid-state UV laser of 355 nm provides a beam that is reflect by mirrors 732 and 734. The mirror 734 directs the beam onto the axis of the NET 122, and the beam is expanded by an expander 736 to be wide enough to encompass the particle of interest while it is trapped in the NET 122. The power, wavelength and bandwidth of the laser are selected to achieve a desired phase and/or temperature for the particle of interest.

Specific experiments to demonstrate the FIG. 1 spectrometer concerned charge distributions in 510 and 990 nm PSL colloids. Electrospray ionization of PSLs produces particles that carry a wide range of elementary charges. The QD selects a subset of these particles for injection into the NET 122 and measurement with ICD2. The Rayleigh limit for a charged liquid governs the maximum charge a particle can acquire when generated by electrospray ionization. To avoid Coulombic explosion, the total charge of a liquid sphere, q, must satisfy:

$$q \leq 8\pi\sqrt{\epsilon_0 \gamma \alpha^3}, \quad (5)$$

where $\epsilon_0$ is the permittivity of free space, $\gamma$ is the surface tension of the liquid, and $\alpha$ is the radius of the liquid droplet. The surface tension can be approximated as the surface tension of a 50:50 $H_2O:CH_3OH$ solution. At the desolvation gas temperature of ~85° C. used in these experiments, the surface tension of this solvent is estimated to be 26.56 mN/m. For the particle sizes studied in the experiments, the Rayleigh limits in these conditions are 9,800 and 26,500 elementary charges, z, for the 510 and 990 nm PSLs, respectively.

Figure 8:
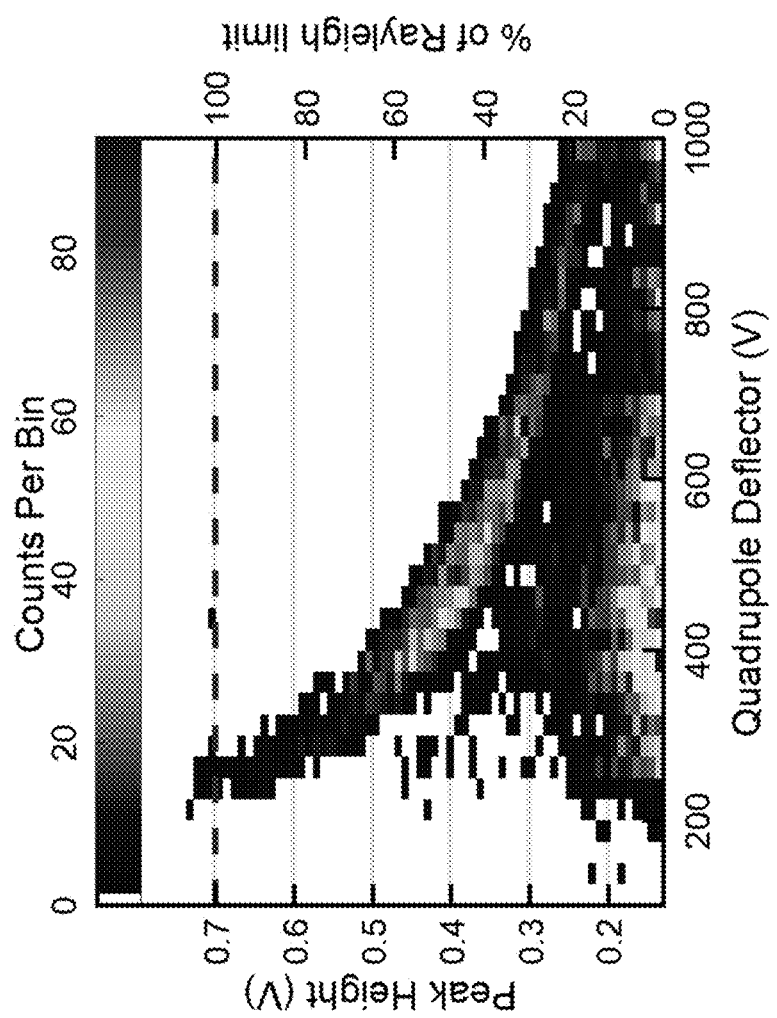

FIG. 8 shows a 2D map of the number of 990 nm PSL particles passing through the ICD-QD2, immediately after the QD 120, plotted against the QD potential and amplitude of the image charge signal for each particle. ICD-QD2 was not calibrated directly, but comparison to charge measurements performed on ICD2 shows that the Rayleigh limit of 26500 charges would correspond to a peak height of 0.7 V on ICD-QD2. The region of interest is the curved band (the large horizontal feature correlated with lower peak heights corresponds to particles that have impacted the surface of ICD-QD2, rather than passing through). The inverse relationship between the amplitude of the image charge signal and QD potential is consistent with particles presenting with a constant total kinetic energy, which in turn is consistent with particles of similar size, travelling at similar velocities. At low QD potentials, particles with a large number of charges are selected, with the number of charges limited by the Rayleigh limit. At high QD potentials, the kinetic energy is partitioned among fewer charges, leading to the detection of correspondingly smaller amplitude image charge signals.

Figure 9:
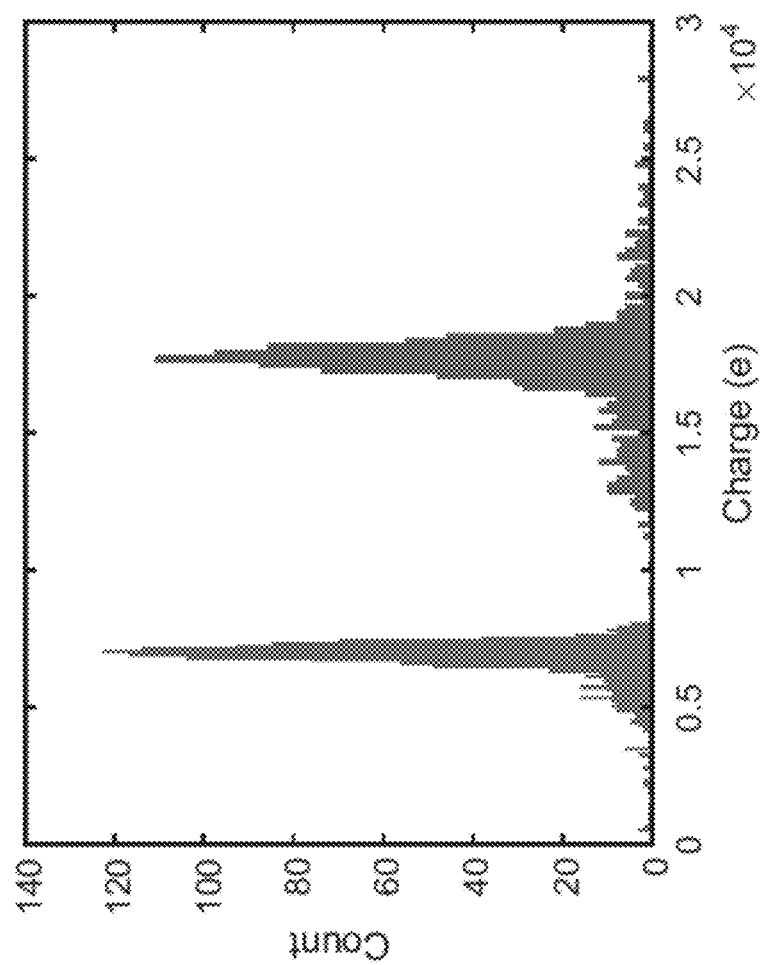
FIG. 9 is experimental data showing Charge distribution of 51 nm PSL and 990 nm PSL species, energy selected for 70 eV/z and 400 eV/z, respectively.
Figure 10:
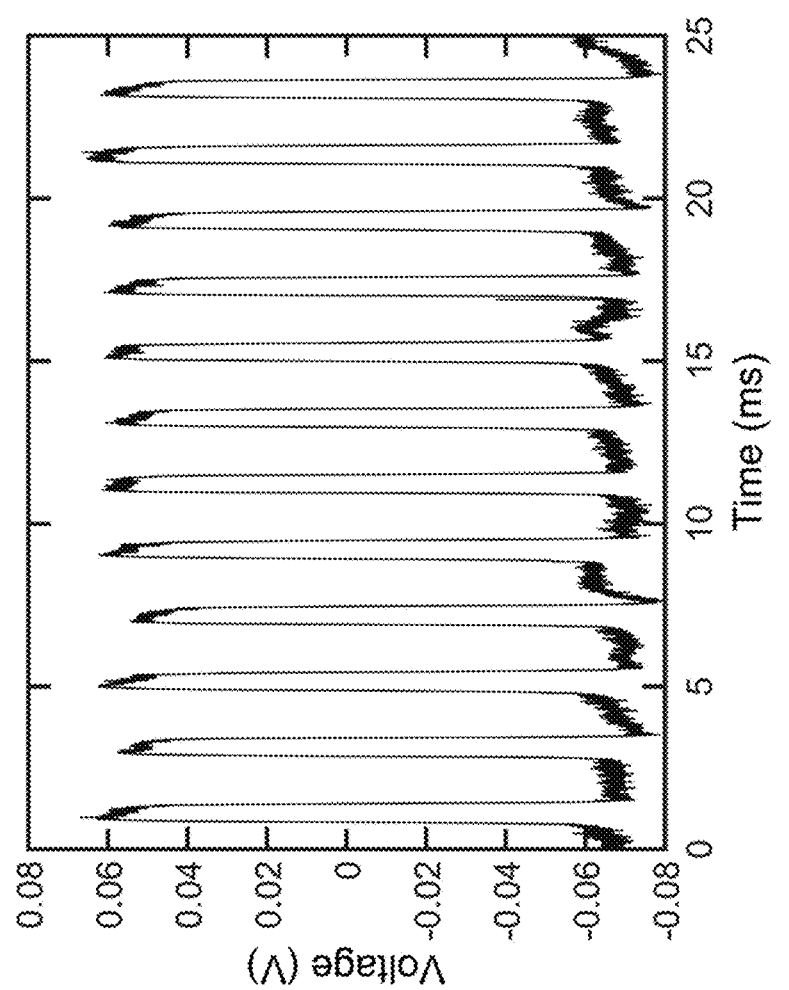
FIG. 10 plots a portion of typical ICD2 trace for a 990 nm PSL oscillating in the NET; Acquisition captures all peaks, overlays them and finds the mean peak height to calculate particle charge.

FIG. 9 shows the measured charge distributions for 510 nm and 990 nm particles. In these measurements, the QD 120 was set to 70 V for selection of 510 nm particles, and to 400 V for 990 nm particles. The charge measurement is performed by calculating the mean peak height in volts of the image charge waveform induced by the trapped particle (FIG. 10) in a 64 ms data acquisition window. The amplitude of the acquired waveform is converted to a measure of charge using the gain calibration factor. These charge measurements fall below the Rayleigh limit for each species and above previous measurements reported for smaller PSLs.

Figure 11:
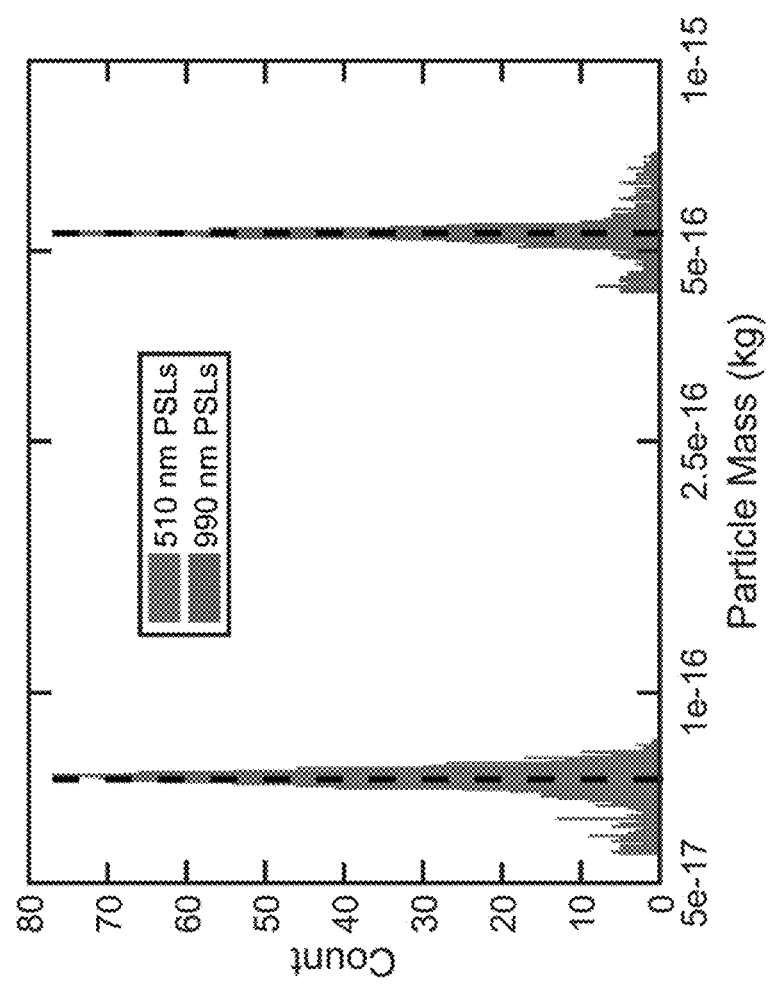
FIG. 11 is data of mass distribution of 510 nm PSL and 990 nm PSL species, with kinetic energies of 70 eV/z and 400 eV/z respectively; expected mass of each species is shown in black (7.295e-17 kg for 510 nm PSLs and 5.336e-16 kg for 990 nm PSLs); for the presented histogram, 510 nm particles whose mass is more than ±1.3σ from the mean are rejected, and 990 nm particles whose mass is more than ±0.8σ from the mean are rejected.

Using equation (1), the measured charge and frequency can be used to calculate the mass of the trapped particles. For the PSL samples studied, the expected mass-per-particle is in the Gigadalton range: 43.9 GDa ($7.3\times10^{-17}$ kg) for 510 nm PSLs, and 321.3 GDa ($5.34\times10^{-16}$ kg) for 990 nm PSLs. These experimental values for the particle mass are in good agreement with the expected values, as shown in FIG. 11 for the particle charge distributions shown in FIG. 9.

With spectrometers in accordance with the invention and the above exemplary embodiments, a wide range of particle final velocities to be achieved. Particles are accelerated/decelerated to a final velocity ($v_f$) according to the following relationship between their initial energy-per-charge ($E_0$), LINAC electrode potential ($E_L$), number of LINAC elements used (n), and initial velocity ($v_i$):

$$\frac{v_f}{v_i} = \sqrt{\frac{E_0 + nE_L}{E_0}}. \quad (6)$$

Figure 12:
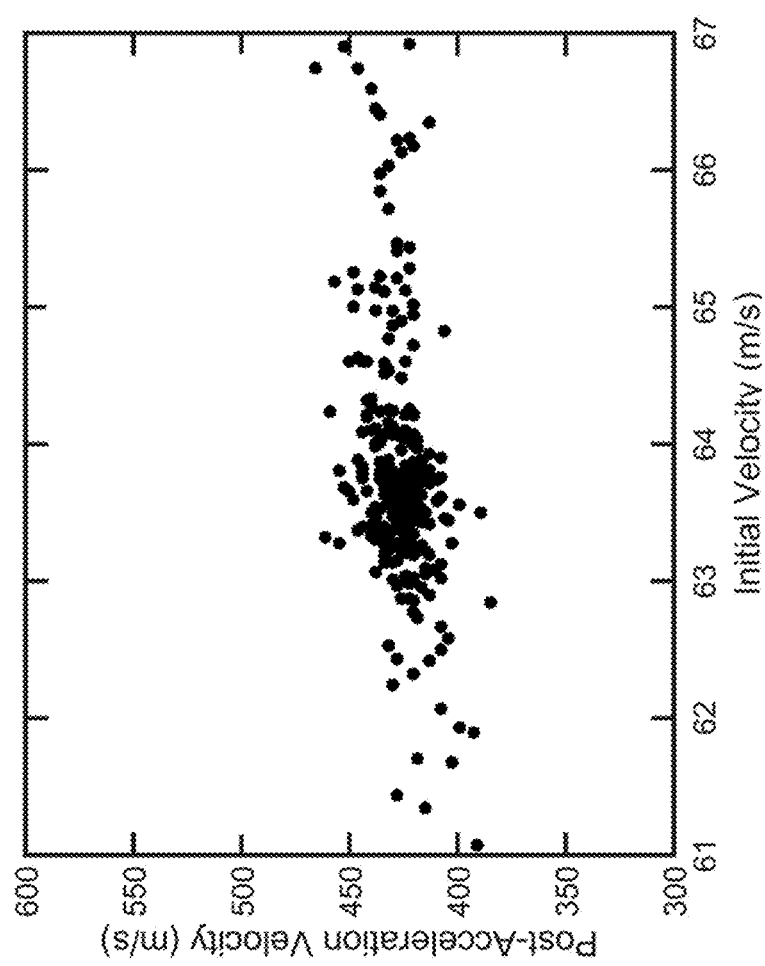
FIG. 12 shows the accelerated velocity distribution for 990 nm PSL particles; Initial energy-per-charge of particles is 400 eV with an acceleration potential of −2500V on each of the of the FIG. 1 LINAC.
Figure 13:
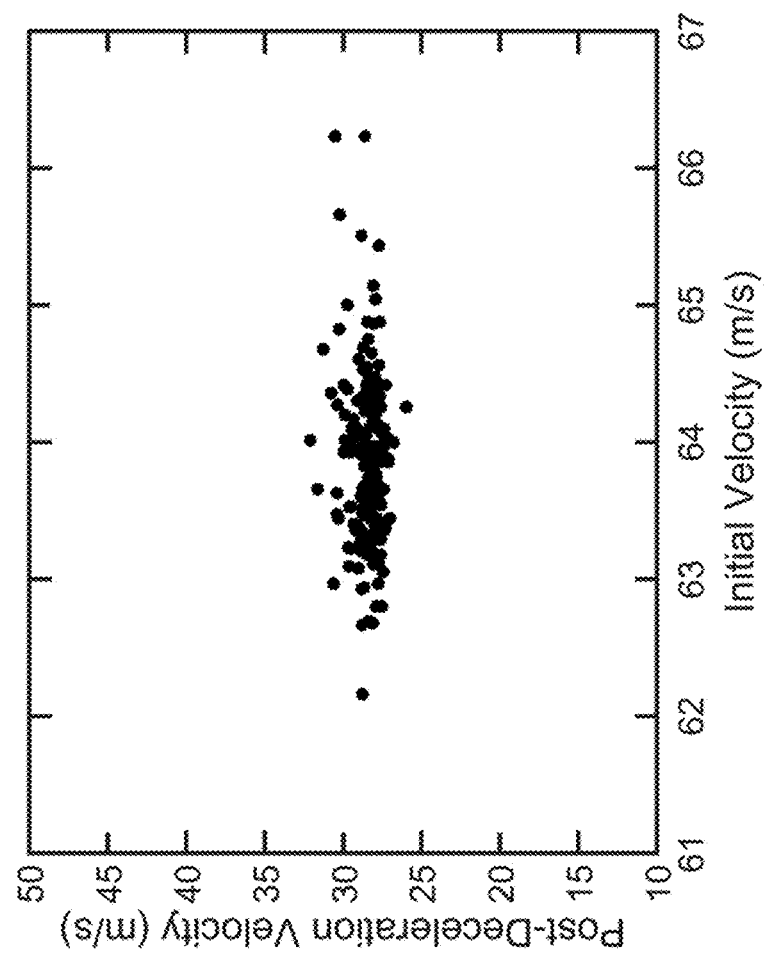
FIG. 13 shows the Decelerated velocity distribution for 990 nm PSL particles. Initial energy-per-charge of particles is 400 eV with a decelerating potential of +35 V on each of the LINAC electrodes.

The initial energy is determined by the potential set on the QD 120, and the initial velocity is determined by the pressure differential across the ADL 106 and the QD 120 chamber. For accelerating voltages, the LINAC electrode potential in the above equation is treated as a positive quantity which results in an increase in final velocity ($v_f > v_i$). When decelerating particles, the LINAC electrode potential is treated as a negative quantity. In the experiments above (using positively charged particles) acceleration was accomplished using negative potentials on the LINAC ranging from 0 V to −45.0 kV (nine stages at −5 kV/stage). Results using an acceleration potential −22.5 kV are shown in FIG. 12. Deceleration of particles was accomplished using positive potentials on the LINAC ranging from 0 V to +383 V (nine stages at 42.5 V/stage). Results using the deceleration potential +315 V are shown in FIG. 13. The apparatus is designed to use voltages up to 20 kV/stage. A terminal velocity of 2.5 km/s would be expected to be reached at 180 kV for the 510 nm PSLs with m/z values used in the present experiments. The number of LINAC stages can be easily extended.

Figure 14:
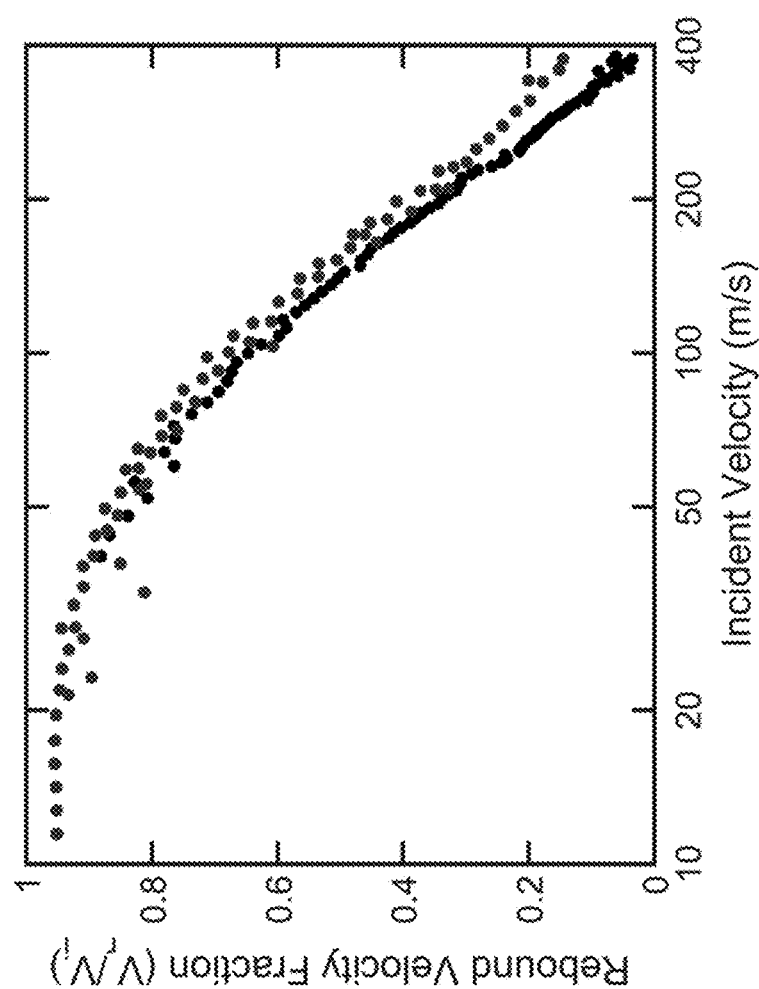
FIG. 14 plots coefficient of restitution data for 510 nm PSLs at normal incidence on silicon, presented with incident velocity grouped in 4 m/s bins then averaged (mean); Any data outside of one standard deviation from the mean for each bin were removed; the data were created from 4348 measured events, and compared to prior work of others.
Figure 15:
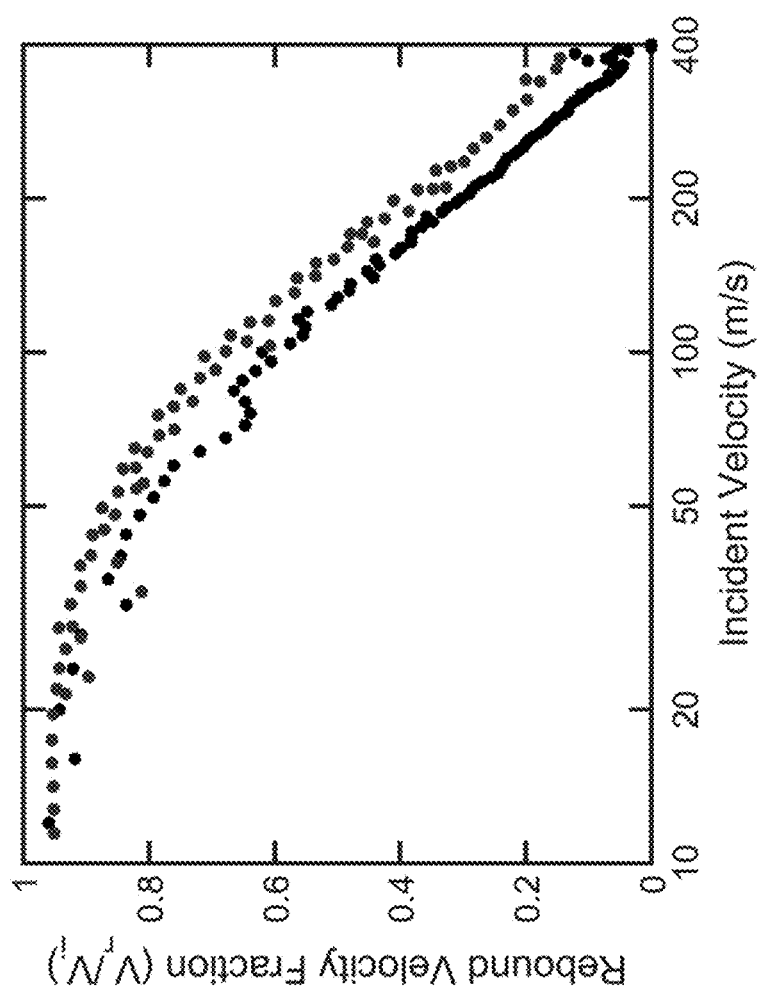
FIG. 15 plots coefficient of restitution data for 990 nm PSLs at normal incidence on silicon, presented with incident velocity grouped in 4 m/s bins then averaged (mean); any data outside of one standard deviation from the mean for each bin were removed; that data were created from 3592 measured events, and compared to prior work of others.

Impact dynamics and the coefficient of restitution for PSL nanoparticles can be determined. In various particle-surface collision models of simple collisions (homogenous particles colliding with a flat surface at normal incidence with no rotation) the coefficient of restitution, e, is an empirical coefficient that fully characterizes the collision. At sufficient distances from the collision surface (to avoid continual particle-surface interaction) e can be defined by:

$$e^2 = 1 - \frac{KE_{incident} - KE_{rebound}}{KE_{incident}} = \left(\frac{v_{rebound}}{v_{incident}}\right)^2; \quad (7)$$

where KE is the kinetic energy of the particle and v is the particle velocity. This is a measure of how the kinetic energy of the particle is partitioned between rebounding kinetic energy and the work of the collision (phonon radiation, target surface waves, plastic deformation of particle, etc.). In general, e can be written as a combination of coefficients associated with each mechanism of irreversible energy loss:

$$e_{tot} = 1 - \Sigma_{m=1}^{m=n}(1 - e_m^2) \quad (8)$$

where $e_{tot}$ is described as a combination of an n number of coefficients each associated with energy loss mechanism m. Due to the complexity in encompassing all possible mechanisms for a given system, no single model exists that accurately predicts a general particle-surface collision. Accordingly, it is valuable to gather coefficient of restitution data for various materials and systems to allow the development of more general models. In FIGS. 14 and 15, the measured coefficients of restitution are presented for 510 nm and 990 nm PSLs impacting along the surface normal on a silicon wafer. The data are compared to results presented by Dahneke (Dahneke B., "Particle bounce or capture—search for an adequate theory: I. Conservation-energy-model for a simple collision process," Aerosol Sci Tech. 1995; 23:25-39; Dahneke B., "Further measurements of the bouncing of small latex spheres," J Coll Int Sci. 1975; 51:58-65) for 1.27 µm PSLs on a fused silica substrate. Deviations are minor and can be attributed to subtle differences in measurement techniques and materials.

The experiments showed the ability for creation, trapping, acceleration/deceleration, and coefficient of restitution measurements of highly-charged submicron particles. Single highly charged PSL spheres were generated with an ESI source. Subsequent trapping and CDMS analysis of individual particles was demonstrated. Individual particle acceleration/deceleration was demonstrated, allowing the acquisition of quantitative coefficient of restitution data. The flexibility of single particle on-the-fly analysis allows the present spectrometer to function with a wide range of micro and nanoparticle masses and charges from a given particle source. Additionally, the variable energy selection of the spectrometer allows a variety of particle sources to be implemented in addition to the demonstrated electrospray ionization, including liquid metal ion sources and needle-charge dust sources. The wide range of final energies achievable with the variable linear accelerator/decelerator enables a variety of scattering experiments to be performed to examine both hypo- and hypervelocity impact phenomena.

In the experiments, an example nanoparticle was the PSL nanoparticle. Additional experiments have been performed with metallic tin particles. The coefficient of restitution of tin particle has been measured on both silicon and molybdenum target surfaces. Additional targets have also been used for measuring coefficient of restitution with both tin and PSL particles. These targets include free standing thin film apertures with thicknesses below 50 nm. The apertures are mounted with a frame that suspends the taunt film in free space along the beam line of the spectrometer. In addition to coefficient of restitution measurements, the velocity at which these films broke was recorded.

Additional experiments have been performed using the spectrometer with solvent crystals and metallic tin particles wherein particles were accelerated to high velocities (>700 m/s) and impacted upon a multichannel plate detector. The particle fragmentation from impact was then imaged using a phosphor screen located behind the multichannel plate stack coupled with an external CCD camera to capture the fragmentation distribution.

While specific embodiments of the present invention have been shown and described, it should be understood that other modifications, substitutions and alternatives are apparent to one of ordinary skill in the art. Such modifications, substitutions and alternatives can be made without departing from the spirit and scope of the invention, which should be determined from the appended claims.

Various features of the invention are set forth in the appended claims.

The invention claimed is:

1. A spectrometer device for analysis of aerosol particles, dusts, and other microparticles and/or nanoparticles, the device comprising an electrospray ionization source supplying a charged particle stream to an aerodynamic lens that focuses and collimates a beam of charged particles; an electrostatic trap with entrance and exit mirrors configured and controlled to accept the beam of charged particles and trap a single trapped charged particle at a time in the electrostatic trap to oscillate with a measurable amplitude and frequency, a sensor for sensing the amplitude and frequency, and a processor for determining a calculated mass to charge ratio from the amplitude and frequency of oscillation of the trapped charged particle in real time.

2. The device of claim 1, further comprising a linear accelerator for accelerating the trapped charged particle toward a target, wherein the trapped charged particle is released into the linear accelerator at a time calculated to achieve a predetermined velocity and timing via subsequent acceleration or deceleration of the trapped charged particle in the linear accelerator given its calculated mass-to-charge ratio.

3. The device of claim 1 wherein the electrospray ionization source is fully enclosed in a controlled atmosphere.

4. The device of claim 1, wherein the electrostatic trap is cooled to control the phase of the trapped charged particle.

5. The device of claim 1, wherein the aerodynamic lens is comprised of a series of apertures machined to particular size and finish.

6. The device of claim 1, further comprising a charge detector after said aerodynamic lens that confirms charged particle presence in the beam.

7. The device of claim 6, further comprising ion optics to select and focus charged particles into said electrostatic trap.

8. The device of claim 1, wherein the mass to charge ratio m/z ratio of the trapped charged particle in the trap is determined by the processor from its oscillation frequency, f, using the following relationship:

$$m/z = \frac{c}{f^2} \qquad (1)$$

wherein the calibration factor C is dependent on trapping potentials and the kinetic energy-per-charge of the trapped charged particle.

9. The device of claim 8, wherein the processor further calculates the velocity of the trapped charged particle in the trap by measuring the temporal width of the output pulses ($t_{pulse\ width}$) from an image charge detector ICD2 of length $L_{ICD2}$:

$$v_{particle} = \frac{t_{pulse\ width}}{L_{ICD_2}}. \qquad (2)$$

10. The device of claim 1, further comprising a linear accelerator after the trap and a collision target after the linear accelerator, wherein the processor calculates the accelerated velocity of the trapped charged particle and determines if the trapped charged particle has rebounded from the collision target, and calculates the rebound velocity of the trapped charged particle from the rebounding peak width.

11. The device of claim 10, wherein the collision target comprises a freestanding film that is imaged upon particle impact for damage or destruction.

12. The device of claim 10, wherein the collision target comprises a multichannel plate detector and particle fragmentation is imaged using a phosphor screen and external camera.

13. The device of claim 10, wherein the processor adjusts the trap to re-calibrate continuously by injecting charge into an image charge detector tube of the trap.

14. The device of claim 1, further comprising a laser beam generator including optics to irradiate the trapped charged particle while it is in the electrostatic trap to control the phase of the particle to a predetermined phase.

15. A method for determining the mass to charge ratio of aerosol particles, dusts, and other microparticles and/or nanoparticles, the method comprising:
creating a focused stream of charged micro or nanoparticles;
trapping a single charged particle at a time from the focused stream in an electrostatic trap;
while the single charged particle is trapped, sensing, in real time, the amplitude and frequency of the oscillation of the single charged particle, and determining the mass to charge ratio of the single charged particle from the amplitude and frequency of oscillation.

16. The method of claim 15, further comprising altering the temperature and/or phase of the single charged particle.

17. The method of claim 16, wherein said altering comprises heating, cooling or freezing of the single charged particle.

18. The method of claim 15, further comprising releasing the single charged particle into a linear accelerator at a time calculated to achieve a predetermined velocity and timing via subsequent acceleration or deceleration of the single charged particle in the linear accelerator given its calculated mass-to-charge ratio.

19. The method of claim 15, further comprising monitoring the collision of the single charged particle emitted from the linear accelerator into a target.

* * * * *